(12) United States Patent
Radford et al.

(10) Patent No.: US 9,700,637 B2
(45) Date of Patent: Jul. 11, 2017

(54) REACTION-BASED FLUORESCENT PROBES FOR DETECTING ZINC

(71) Applicant: Massachusetts Institute of Technology, Cambridge, MA (US)

(72) Inventors: Robert J. Radford, Durham, NC (US); Stephen J. Lippard, Cambridge, MA (US); Wen Chyan, Denton, TX (US)

(73) Assignee: Massachusetts Institute of Technology, Cambridge, MA (US)

( * ) Notice: Subject to any disclaimer, the term of this patent is extended or adjusted under 35 U.S.C. 154(b) by 58 days.

(21) Appl. No.: 14/783,456

(22) PCT Filed: Apr. 28, 2014

(86) PCT No.: PCT/US2014/035673
§ 371 (c)(1),
(2) Date: Oct. 9, 2015

(87) PCT Pub. No.: WO2014/176591
PCT Pub. Date: Oct. 30, 2014

(65) Prior Publication Data
US 2016/0030598 A1     Feb. 4, 2016

Related U.S. Application Data

(60) Provisional application No. 61/816,291, filed on Apr. 26, 2013.

(51) Int. Cl.
| | |
|---|---|
| *A61K 49/00* | (2006.01) |
| *C07D 405/14* | (2006.01) |
| *G01N 33/58* | (2006.01) |
| *A61B 5/00* | (2006.01) |
| *A61B 5/145* | (2006.01) |
| *C07D 311/16* | (2006.01) |
| *C07D 493/10* | (2006.01) |
| *C07F 9/54* | (2006.01) |
| *C07F 3/06* | (2006.01) |
| *G01N 33/84* | (2006.01) |
| *A61B 5/1455* | (2006.01) |

(52) U.S. Cl.
CPC ........ *A61K 49/0039* (2013.01); *A61B 5/0071* (2013.01); *A61B 5/1455* (2013.01); *A61B 5/14546* (2013.01); *A61B 5/4041* (2013.01); *A61B 5/4064* (2013.01); *A61B 5/425* (2013.01); *A61B 5/4381* (2013.01); *C07D 311/16* (2013.01); *C07D 405/14* (2013.01); *C07D 493/10* (2013.01); *C07F 3/06* (2013.01); *C07F 9/5442* (2013.01); *G01N 33/582* (2013.01); *G01N 33/84* (2013.01)

(58) Field of Classification Search
CPC ..... A61K 49/00; C07D 215/40; C07D 405/14
See application file for complete search history.

(56) References Cited

U.S. PATENT DOCUMENTS

2002/0106697 A1*    8/2002    Lippard ................. C09B 11/08
                                                                                                       435/7.2

OTHER PUBLICATIONS

International Search Report dated Aug. 4, 2014, from PCT/US14/35673.

* cited by examiner

*Primary Examiner* — Michael G Hartley
*Assistant Examiner* — Jagadishwar Samala
(74) *Attorney, Agent, or Firm* — Dana M. Gordon; Foley Hoag LLP

(57) ABSTRACT

Disclosed are compounds and methods useful in the detection of e.g., $Zn^{2+}$, in vitro and in vivo. The compounds include amino acids and peptides functionalized with a moiety that binds, e.g., $Zn_{2+}$. Importantly, the compounds do not exhibit substantial fluorescence in the absence of zinc.

22 Claims, 20 Drawing Sheets

| Sensor | Turn-on | $\Phi_{apo}$ | $\Phi_{Zn}$ | $K_D$ | Log $P$ | Charge |
|---|---|---|---|---|---|---|
| ZP1-TPP | 7 | 0.15 | 0.75 | 0.6 nM | -0.11 | – |
| DA-ZP1-TPP | > 140 | < 1% | 0.75 | 5 nM | 0.75 | +1 |

6-CO$_2$H ZP1
Zn:$K_d$~ 0.2nM
DR$^e$: 2.5

6-CO$_2$H Me$_2$ZP1
Zn:$K_d$~ 3 nM
DR: 4

6-CO$_2$H Me$_4$ZP1
Zn:$K_d$~ 600 nM
DR: 2.5

6-CO$_2$H QZ2
Zn:$K_d$~ 40 μM
DR: 150

5. ZPP1

REACTION-BASED FLUORESCENT PROBES FOR DETECTING ZINC

RELATED APPLICATIONS

This application is the National Stage application of PCT/US14/035673, filed Apr. 28, 2014, which claims the benefit of priority to U.S. Provisional Patent Application Ser. No. 61/816,291, filed Apr. 26, 2013.

GOVERNMENT SUPPORT

This invention was made with Government support under Grant No. R01 GM065519 awarded by the National Institutes of Health. The government has certain rights in this invention.

BACKGROUND OF THE INVENTION

Role of Mobile Zinc in Neurobiology

Zinc is the second most abundant metal ion in living systems. Its biological importance is accentuated by the fact that approximately 10% of the human genome is dedicated to the zinc proteome. Whereas the majority of zinc is highly regulated and tightly bound within protein scaffolds, a growing body of evidence suggests the presence of readily exchangeable or "mobile" zinc ("mZn") located within the pancreas, prostate, and brain. The importance of mZn in human health has been extensively documented, but knowledge of its physiology and pathology is incomplete.

Fluorescent-based probes are the most common agents utilized to image mobile zinc within cellular environments. Broadly speaking, zinc probes are divided into two categories: small molecule ("SM") sensors; and genetically encoded ("GE") sensors. SM-based probes offer a scaffold that is readily modified, providing sensors with chemical and physical properties that can be tuned for specific applications. On occasion SM probes can also display unpredictable subcellular distribution, which has led to controversy and confusion in biological communities. Conversely, GE sensors offer impressive control over the subcellular localization of the probe and are inherently biocompatible. Yet, GE probes suffer from the limited tunability of their metal-binding motifs, large sizes, and requirement of complex procedures for their incorporation into mammalian cells.

Metal ions are essential reactive cofactors, obligatory for carrying out complex chemical processes vital to cell metabolism. Yet, the reactive nature of metal ions requires tight regulation of their concentrations and cellular distribution. When unregulated, mobile metal ions have been implicated in multiple neurological disorders, including Alzheimer's disease and amyotrophic lateral sclerosis (ALS).

In this context, it is surprising that large concentrations of mZn (~0.5 mM) occur in regions of the brain containing neuron cell bodies. Although most of this zinc is "static"— i.e., tightly associated with a protein scaffold and serving both as structural and functional components in protein biochemistry—the existence of pools of mZn implies a functional role in neurological biochemistry. Zinc levels in the brain are non-uniformly distributed, with high concentrations occurring in the hippocampus, amygdala, and olfactory bulb.

Observations from the mossy fiber (mf) axons in the CA3 region of the hippocampus—an area of the brain responsible for learning and memory—suggested that the underlying mechanism behind zinc neurochemistry is both complex and nuanced. Zinc released from glutamatergic synaptic vesicles has been proposed to associate with zinc permeable gated channels, including N-methyl-D-aspartate (NMDA) receptors, voltage-gated calcium channels, and the calcium-permeable AMPA (α-amino-3-hydroxy-5-methyl-4-isoxazole propionic)/kainate channel ($Ca^{2+}$-A/K), where it can enter postsynaptic axons and/or function to inhibit postsynaptic mossy fiber long-term potentiation (mf-LTP). Portions of the released zinc have also been proposed to "re-enter" presynaptic termini through calcium-gated ion channels. Upon re-entry, zinc can transactivate the tyrosine kinase receptor (TrkB), independent of neurotrophins, initializing a chain of molecular events critical to both presynaptic mf-LTP and neuronal plasticity. This "dual action" of vesicular zinc appears to be critical in regulating the effectiveness of mf-CA3 synapses and ensuring proper hippocampal function in health and disease, but the mechanistic details of its actions remain incomplete and highly debated.

Imaging and Quantifying Mobile Zinc

Divalent zinc is a good Lewis acid, redox inactive under physiological conditions, and able to adopt multiple binding geometries. Its $d^{10}$ closed-shell electronic structure renders zinc spectroscopically silent, complicating noninvasive in vivo imaging. Currently, fluorescent probes provide the most facile way to image zinc within a cellular environment.

One such family of zinc probes is the ZinPyr (ZP) family of sensors. ZP1 is based on a fluorescein platform that is further modified with two dipicolylamine (DPA) "metal-binding arms," which function to quench fluorescein emissions via photoinduced electron transfer (PET) in the metal-free form. Upon coordination to zinc, the electronic configuration of ZP1 changes, resulting in an attenuation of the PET effect and recovery of fluorescein emissive properties. ZP1 has several attributes that make it a model probe: (1) it is formed in a high yielding, "one-pot" Mannich reaction between 2',7'-dichlorofluorescein and the iminium ion condensation product of formaldehyde and DPA; (2) it is a zinc selective "turn on" sensor, meaning it is non-responsive to the presence of other biologically relevant metal ions such as $Ca^{2+}$, $Mg^{2+}$, $Mn^{2+}$, $Cu^{2+}$, or $Fe^{2+}$; and (3) it is excitable with visible (~500 nm) light, making it compatible with the 488 nm argon line of most fluorescence microscopes, as well as reducing background fluorescence attributed to biological auto-fluorescence. To date, a library of sensors in the ZP family, and an extensive group of related ZS, QZ and ZPP derivatives have been synthesized, allowing access to probes with a wide range of zinc-binding affinities and dynamic ranges. The ZP family of probes has been well documented to function in cellular systems, such as HeLa, hippocampal slices, and pancreatic β-insulinoma cells, and even in live animals (TRAMP—a mouse model of prostate cancer), demonstrating the practical utility of the probes in addressing biological questions.

There exists a need for a new class of sensors for the detection of biological zinc.

SUMMARY OF THE INVENTION

In certain embodiments, the invention relates to a compound represented by Formula 1 or Formula 2 or Formula 3:

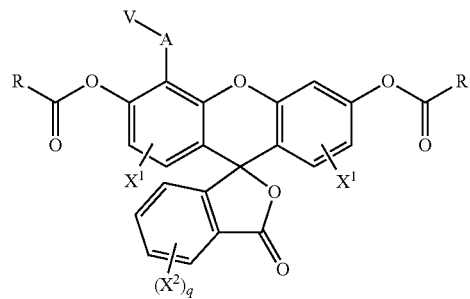

Formula 1

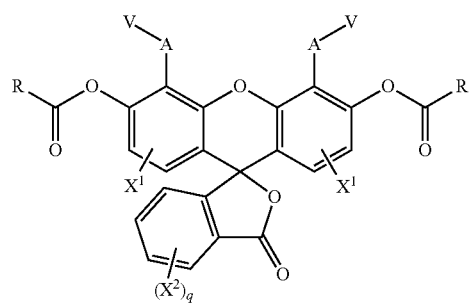

Formula 2

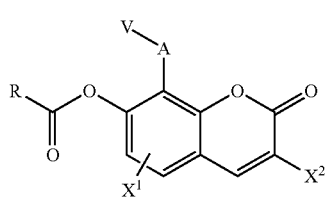

Formula 3 wherein, independently for each occurrence, $X^1$ is —H, —F, or —Cl;

$X^2$ is —F, —Cl, —CO$_2$R$^1$, —C(O)-linker, -linker, —NR$^1$-linker, or —S-linker, wherein the linker, when present, is a linker to a first amino acid or a lipophilic group;

R is alkyl or aryl;

$R^1$ is —H or alkyl;

q is 0, 1, 2, 3, or 4;

A is an alkylene group; and

V is a Lewis base.

In certain embodiments, the invention relates to a compound selected from the group consisting of

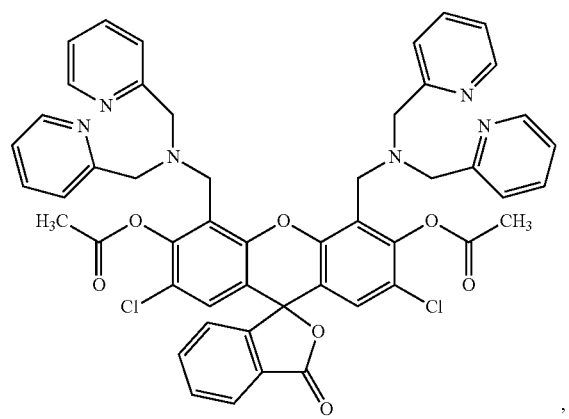

,

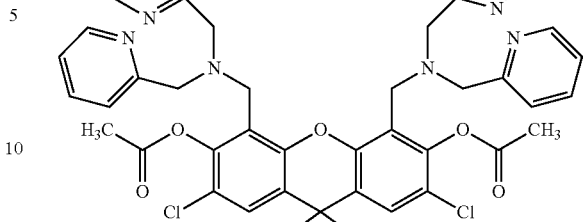

,

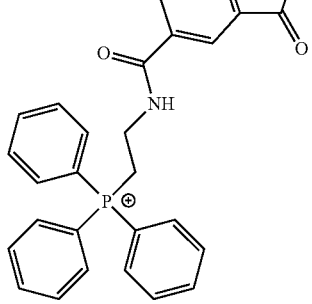

,

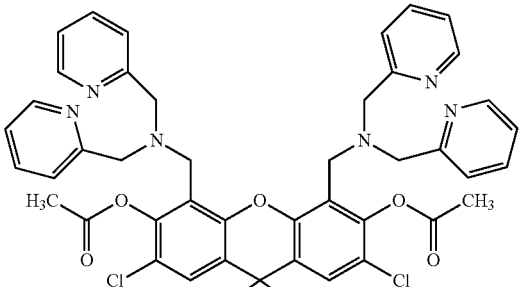

, and

-continued

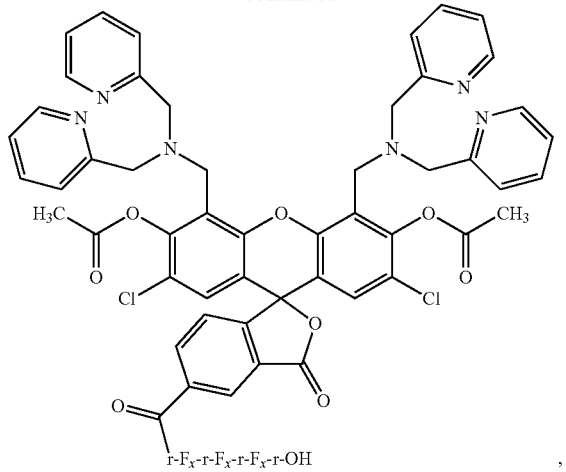

r-F$_x$-r-F$_x$-r-F$_x$-r-OH wherein r is D-arginine; and F$_x$ is L-cyclohexylalanine.

In certain embodiments, the invention relates to a method of quantifying an amount of a substance in a cell, comprising the steps of:
  contacting the cell with a detectable amount of any one of the aforementioned compounds; and
  detecting a signal, wherein the signal emitted by the compound in the presence of the substance is different than the signal emitted by the compound in the absence of the substance.

In certain embodiments, the invention relates to a method of quantifying an amount of a substance in a specific locale of a cell, comprising the steps of:
  contacting the cell with a detectable amount of any one of the aforementioned compounds; and
  detecting a signal from a specific locale of the cell, wherein the signal emitted by the compound in the presence of the substance is different than the signal emitted by the compound in the absence of the substance.

In certain embodiments, the invention relates to a method of quantifying an amount or determining a location of a substance in a subject, comprising the steps of:
  administering to the subject a detectable amount of any one of the aforementioned compounds; and
  detecting a signal, wherein the signal emitted by the compound in the presence of the substance is different than the signal emitted by the compound in the absence of the substance.

DETAILED DESCRIPTION OF THE INVENTION

Overview

Figure 8:
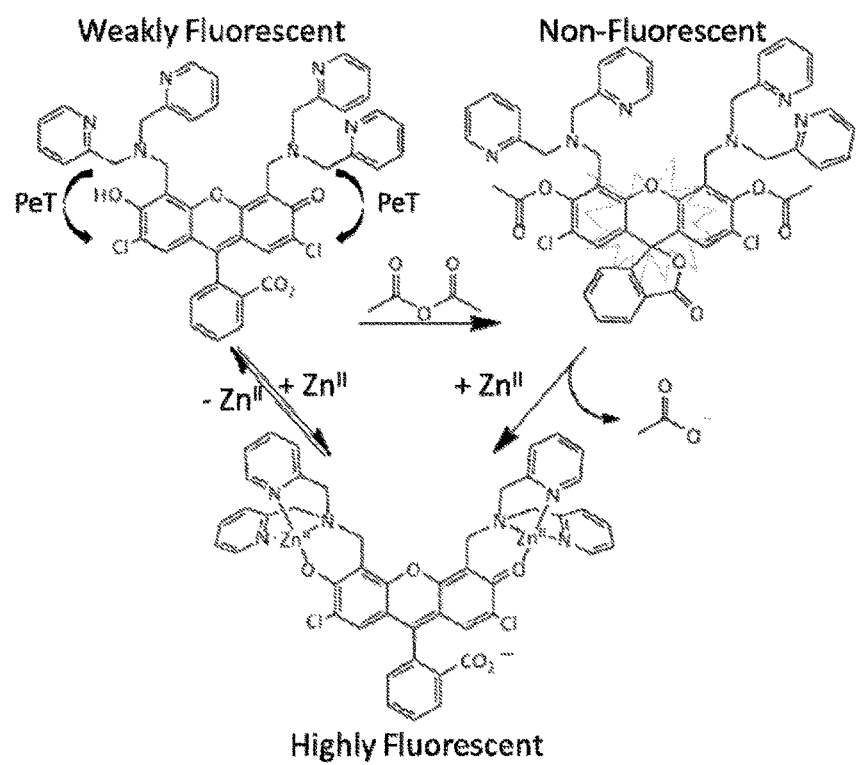
FIG. 8 depicts a schematic, showing that ZP1 can be transformed into the non-fluorescent DA-ZP1 by addition of acetate groups onto the phenolic oxygens of the fluorescein scaffold (top). Coordination of zinc results in zinc-mediated hydrolysis of the ester groups, and a large increase in emission (right). Subsequent removal of the zinc(II) ions diminishes the fluorescence intensity due to PeT from the dipicolylamine groups (left).

In certain embodiments, the invention relates to a reaction-based fluorescent probe for the detection of biological zinc. In certain embodiments, the compounds are esterified (e.g., acetylated) sensors, such as esterified ZP1. In certain embodiments, the esterified compounds are substantially non-fluorescent. In certain embodiments, the esterified compounds are "pro-sensors" (see, e.g., FIG. 8, top). Upon binding zinc, the ester is hydrolyzed via a zinc-mediated process, resulting in restoration of fluorescence (FIG. 8, right). In certain embodiments, the sensor is reversible; that is, when zinc is removed, the fluorescent signal from the fluorophore may be quenched by a photoinduced electron transfer (PeT) mechanism. In certain embodiments, the PeT quenching originates from the dipicolylamine (DPA) metal-binding moieties (FIG. 8, left).

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

Exemplary Compounds

In certain embodiments, the invention relates to a compound represented by Formula 1 or Formula 2 or Formula 3:

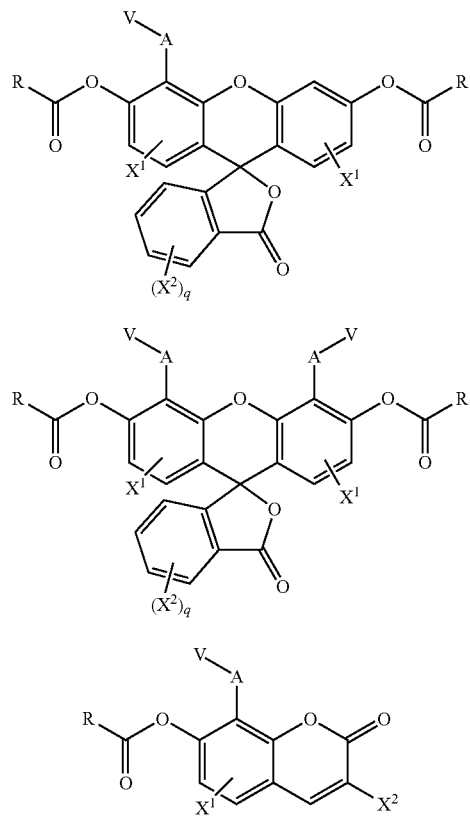

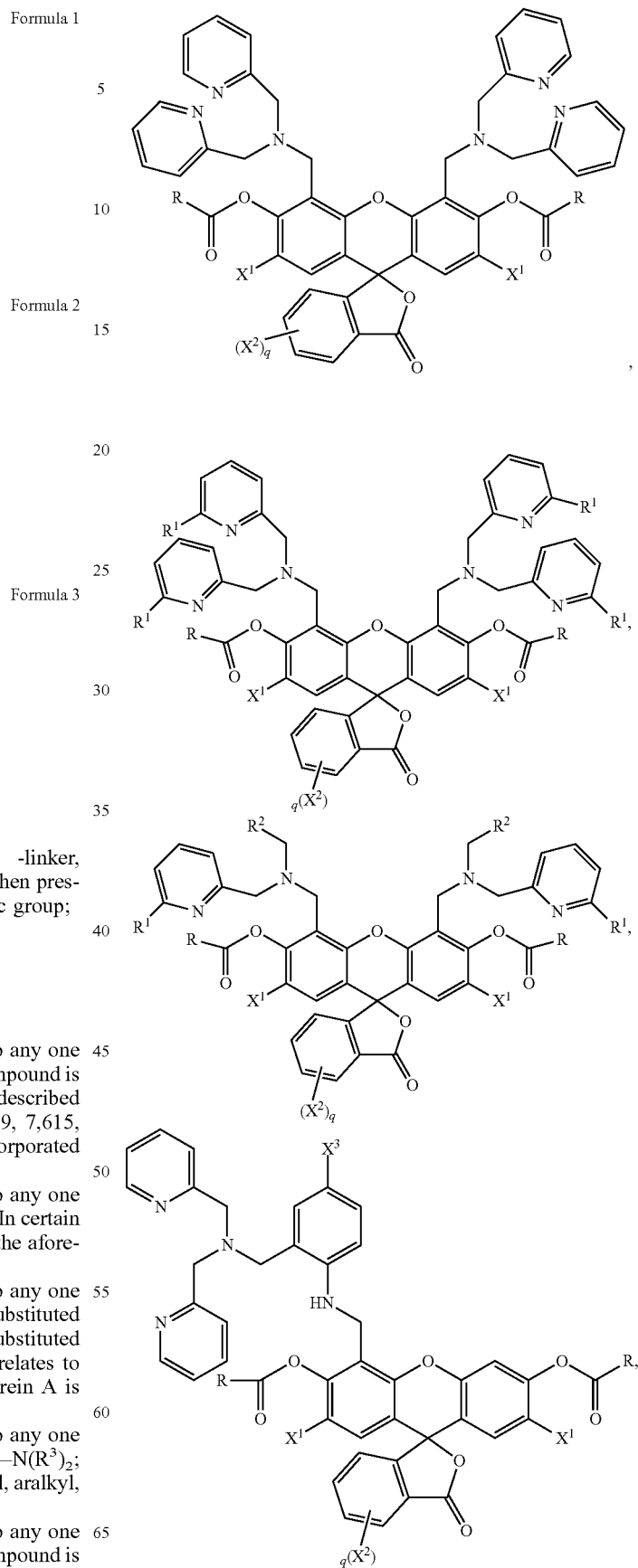

wherein, independently for each occurrence, $X^1$ is —H, —F, or —Cl;

$X^2$ is —F, —Cl, —CO$_2$R$^1$, —C(O)-linker, -linker, —NR$^1$-linker, or —S-linker, wherein the linker, when present, is a linker to a first amino acid or a lipophilic group;

R is alkyl or aryl;

$R^1$ is —H or alkyl;

q is 0, 1, 2, 3, or 4;

A is an alkylene group; and

V is a Lewis base.

In certain embodiments, the invention relates to any one of the aforementioned compounds, wherein the compound is an ester derivative of any one of the compounds described in U.S. Pat. Nos. 7,160,732, 7,018,840, 7,399,639, 7,615,377, 7,488,820, or 7,494,821, all of which are incorporated by reference in their entireties.

In certain embodiments, the invention relates to any one of the aforementioned compounds, wherein q is 0. In certain embodiments, the invention relates to any one of the aforementioned compounds, wherein q is 1.

In certain embodiments, the invention relates to any one of the aforementioned compounds, wherein A is substituted or unsubstituted methylene or substituted or unsubstituted ethylene. In certain embodiments, the invention relates to any one of the aforementioned compounds, wherein A is unsubstituted methylene.

In certain embodiments, the invention relates to any one of the aforementioned compounds, wherein V is —N(R$^3$)$_2$; and R$^3$ is independently —H, alkyl, aryl, heteroaryl, aralkyl, heteroaralkyl, alkoxyalkyl, or alkylthioalkyl.

In certain embodiments, the invention relates to any one of the aforementioned compounds, wherein the compound is selected from the group consisting of

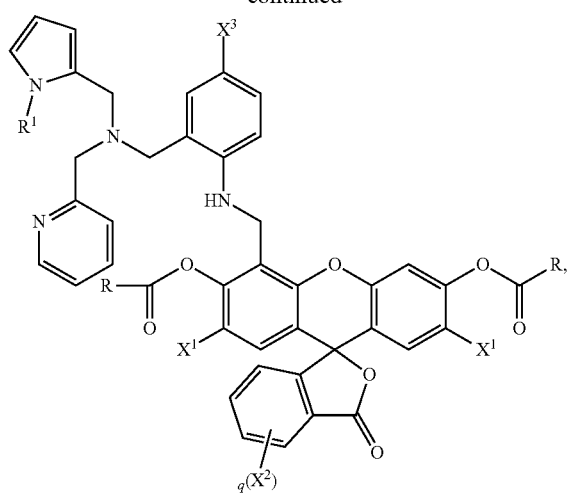
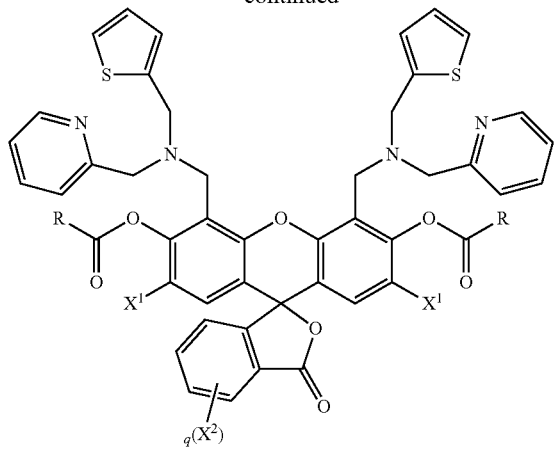
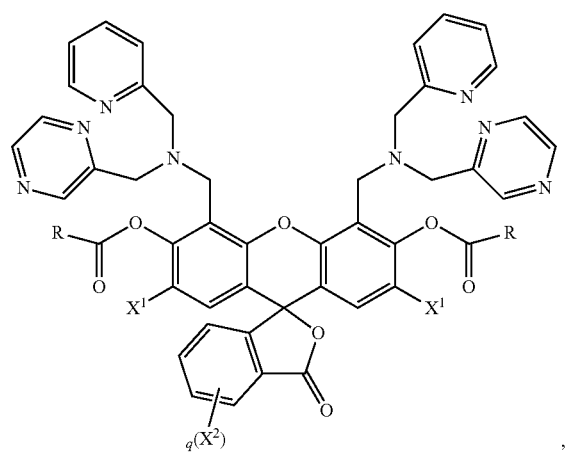
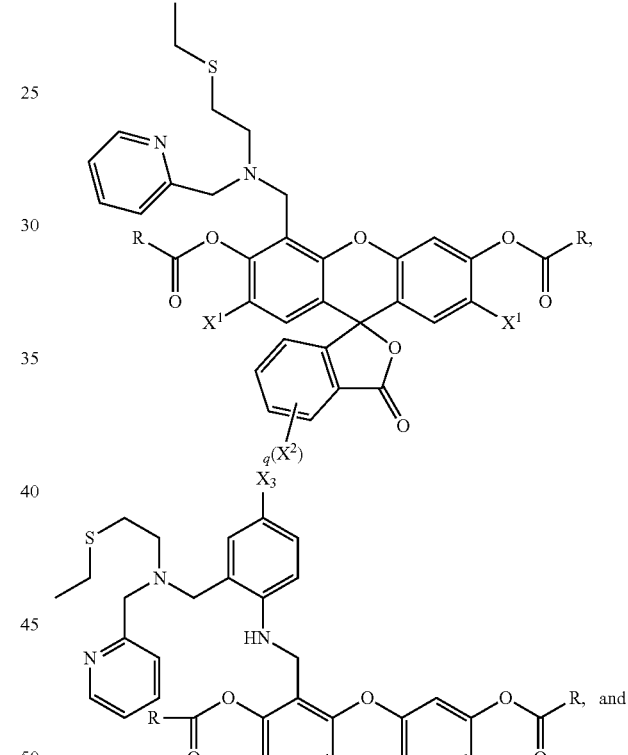
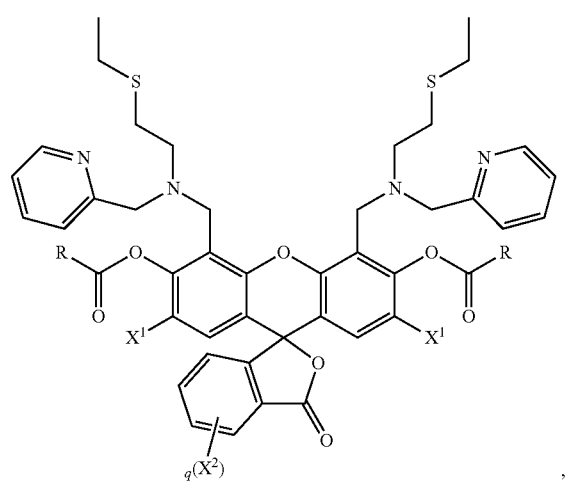
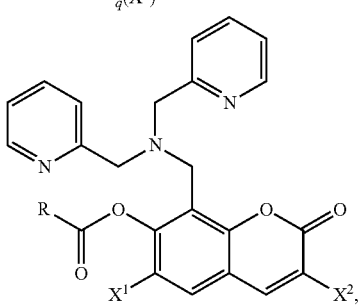

wherein, independently for each occurrence, $X^1$ is —H, —F, or —Cl;

$X^2$ is —F, —Cl, —CO$_2$R', —C(O)-linker, -linker, —NR$^1$-linker, or —S-linker, wherein the linker, when present, is a linker to a first amino acid or a lipophilic group;

$X^3$ is —H, —F, —Cl, or —OR$^1$;

R is alkyl or aryl;

R$^1$ is —H or alkyl; and

R$^2$ is —H or phenyl.

In certain embodiments, the invention relates to any one of the aforementioned compounds, wherein $X^1$ is —H. In certain embodiments, the invention relates to any one of the aforementioned compounds, wherein $X^1$ is —Cl.

In certain embodiments, the invention relates to any one of the aforementioned compounds, wherein q is 1; and $X^2$ is —C(O)-linker.

In certain embodiments, the invention relates to any one of the aforementioned compounds, wherein R is alkyl. In certain embodiments, the invention relates to any one of the aforementioned compounds, wherein R is methyl, ethyl, propyl, or butyl. In certain embodiments, the invention relates to any one of the aforementioned compounds, wherein R is methyl.

In certain embodiments, the invention relates to any one of the aforementioned compounds, wherein the compound is:

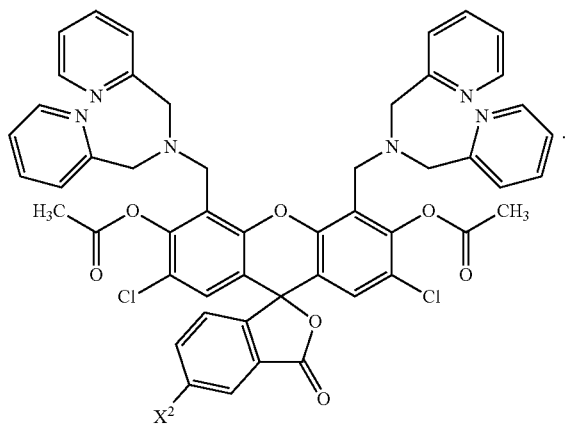

In certain embodiments, the invention relates to any one of the aforementioned compounds, wherein the compound is:

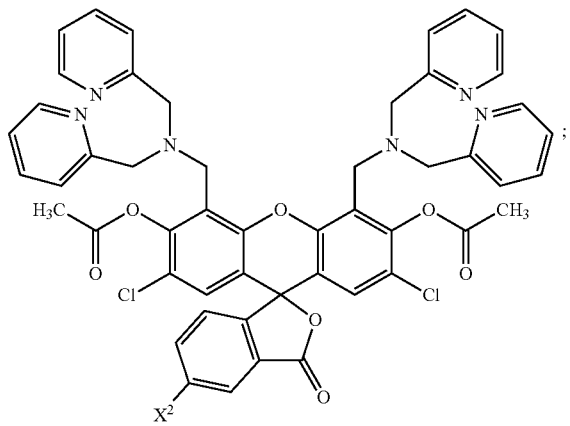

and $X^2$ is —C(O)-linker.

In certain embodiments, the invention relates to any one of the aforementioned compounds, wherein the first amino acid is a natural α-amino acid or a non-natural α-amino acid.

In certain embodiments, the invention relates to any one of the aforementioned compounds, wherein the first amino acid is a natural α-amino acid.

In certain embodiments, the invention relates to any one of the aforementioned compounds, wherein the first amino acid is a non-natural α-amino acid.

In certain embodiments, the invention relates to any one of the aforementioned compounds, wherein the first amino acid is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, 2,3-diaminopropionic acid (DAP), or cyclohexylalanine.

In certain embodiments, the invention relates to any one of the aforementioned compounds, wherein the first amino acid is arginine. In certain embodiments, the invention relates to any one of the aforementioned compounds, wherein the first amino acid is D-arginine.

In certain embodiments, the invention relates to any one of the aforementioned compounds, wherein the linker is an amide bond, a disulfide bond, a thioether bond, a thiourea, or a triazole.

In certain embodiments, the invention relates to any one of the aforementioned compounds, wherein the linker is an amide bond.

In certain embodiments, the invention relates to any one of the aforementioned compounds, wherein the compound is:

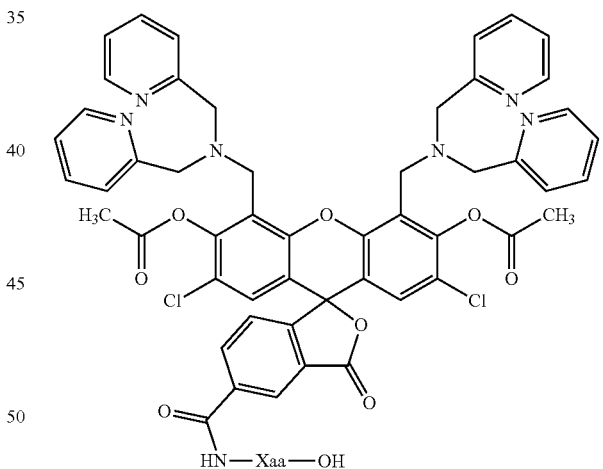

wherein Xaa is a natural amino acid or a non-natural amino acid.

In certain embodiments, the invention relates to any one of the aforementioned compounds, wherein Xaa is a natural α-amino acid or a non-natural α-amino acid.

In certain embodiments, the invention relates to any one of the aforementioned compounds, wherein Xaa is a natural α-amino acid.

In certain embodiments, the invention relates to any one of the aforementioned compounds, wherein Xaa is a non-natural α-amino acid.

In certain embodiments, the invention relates to any one of the aforementioned amino acid compounds, wherein Xaa is arginine.

In certain embodiments, the invention relates to a compound selected from the group consisting of

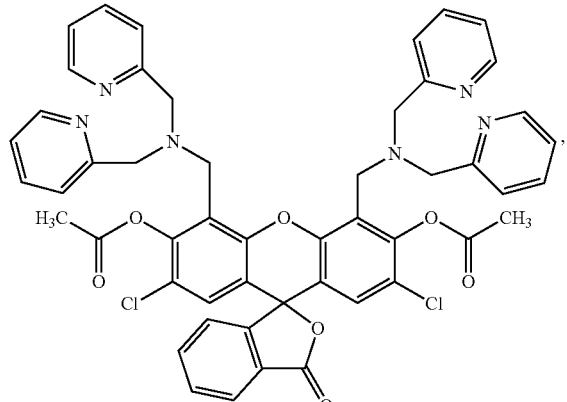

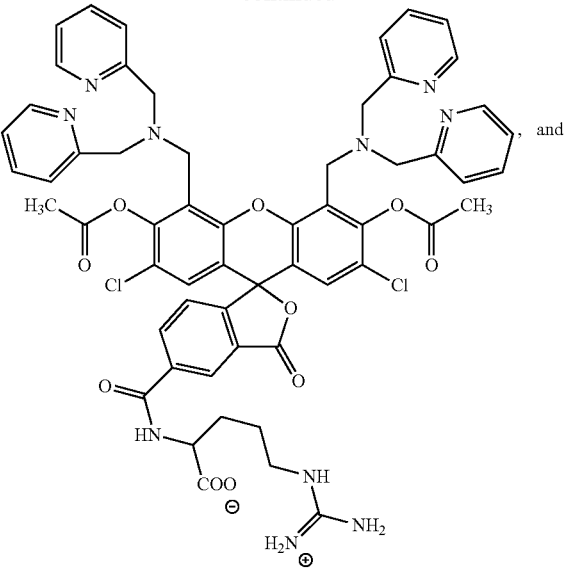

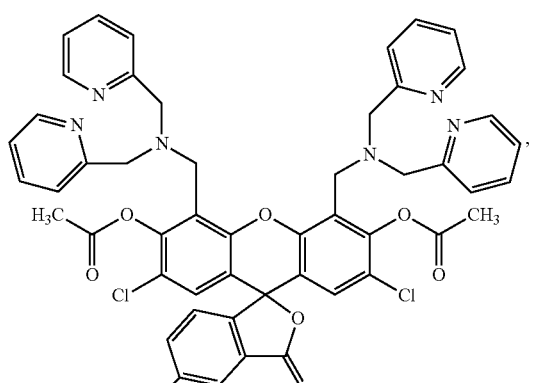

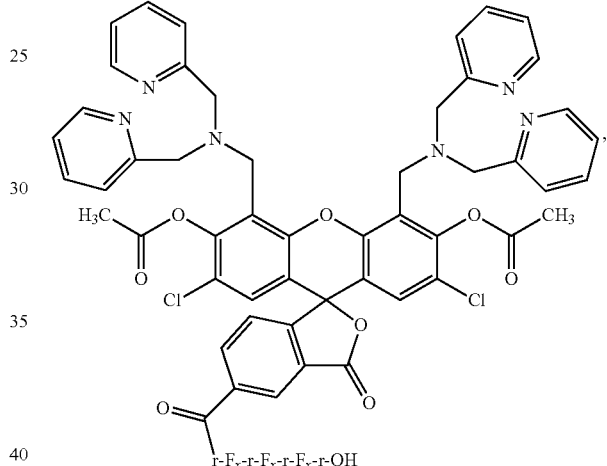

r-F$_x$-r-F$_x$-r-F$_x$-r-OH wherein r is D-arginine; and F$_x$ is L-cyclohexylalanine.

Exemplary Methods of Use

In certain embodiments, the invention relates to a method of quantifying an amount of a substance in a cell, comprising the steps of:
  contacting the cell with a detectable amount of any one of the aforementioned compounds; and
  detecting a signal, wherein the signal emitted by the compound in the presence of the substance is different than the signal emitted by the compound in the absence of the substance.

In certain embodiments, the invention relates to a method of quantifying an amount of a substance in a specific locale of a cell, comprising the steps of:
  contacting the cell with a detectable amount of any one of the aforementioned compounds; and
  detecting a signal from a specific locale of the cell, wherein the signal emitted by the compound in the presence of the substance is different than the signal emitted by the compound in the absence of the substance.

In certain embodiments, the invention relates to any one of the aforementioned methods, further comprising the step of:

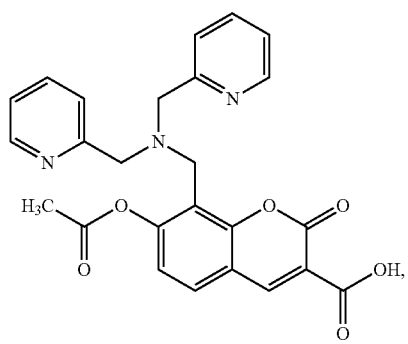

irradiating the cell in the presence of the compound at a wavelength for a period of time.

In certain embodiments, the invention relates to any one of the aforementioned methods, further comprising the steps of:
    exposing to a first magnetic field the cell in the presence of the compound for a first period of time; and
    exposing to an electromagnetic field the cell in the presence of the compound at a second frequency for a second period of time, wherein the second frequency is a radio frequency.

In certain embodiments, the invention relates to any one of the aforementioned methods, wherein the specific locale in the cell is an intracellular probe, an extracellular probe, a trans-Golgi network, a mitochondrion, or an endoplasmic reticulum.

In certain embodiments, the invention relates to any one of the aforementioned methods, wherein the cell is a HeLa cell, a HEK cell, or a neuron.

In certain embodiments, the invention relates to any one of the aforementioned methods, wherein the signal is detected using ratiometric fluorescence microscopy.

In certain embodiments, the invention relates to a method of quantifying an amount or determining a location of a substance in a subject, comprising the steps of:
    administering to the subject a detectable amount of any one of the aforementioned compounds; and
    detecting a signal, wherein the signal emitted by the compound in the presence of the substance is different than the signal emitted by the compound in the absence of the substance.

In certain embodiments, the invention relates to any one of the aforementioned methods, wherein the method is a method of quantifying the amount or determining the location of a substance released from the hippocampus; and the substance is $Zn^{2+}$.

In certain embodiments, the invention relates to any one of the aforementioned methods, wherein the method is a method of quantifying the amount or determining the location of a substance released from the CA3 region of the hippocampus; and the substance is $Zn^{2+}$.

In certain embodiments, the invention relates to any one of the aforementioned methods, wherein the method is a method of quantifying the amount or determining the location of a substance released from presynaptic mossy fibers (mf) in the CA3 region of the hippocampus; and the substance is $Zn^{2+}$.

In certain embodiments, the invention relates to any one of the aforementioned methods, wherein the location of the substance is the synaptic cleft.

In certain embodiments, the invention relates to any one of the aforementioned methods, wherein the location of the substance is the intracellular space of the hippocampus.

In certain embodiments, the invention relates to any one of the aforementioned methods, wherein the location of the substance is in mossy fiber buttons of the hippocampus.

In certain embodiments, the invention relates to any one of the aforementioned methods, wherein the location of the substance is the pancreas.

In certain embodiments, the invention relates to any one of the aforementioned methods, wherein the location of the substance is the prostate.

In certain embodiments, the invention relates to any one of the aforementioned methods, wherein the location of the substance is the prostatic fluid.

In certain embodiments, the invention relates to any one of the aforementioned methods, wherein the subject is a mammal.

In certain embodiments, the invention relates to any one of the aforementioned methods, wherein the subject is a mouse or a rat.

In certain embodiments, the invention relates to any one of the aforementioned methods, wherein the signal is fluorescence.

In certain embodiments, the invention relates to any one of the aforementioned methods, wherein the signal is detected using ratiometric fluorescence microscopy.

In certain embodiments, the invention relates to any one of the aforementioned methods, wherein the substance is $Zn^{2+}$.

EXEMPLIFICATION

The invention now being generally described, it will be more readily understood by reference to the following examples, which are included merely for purposes of illustration of certain aspects and embodiments of the invention, and are not intended to limit the invention.

Example 1

Figure 1:
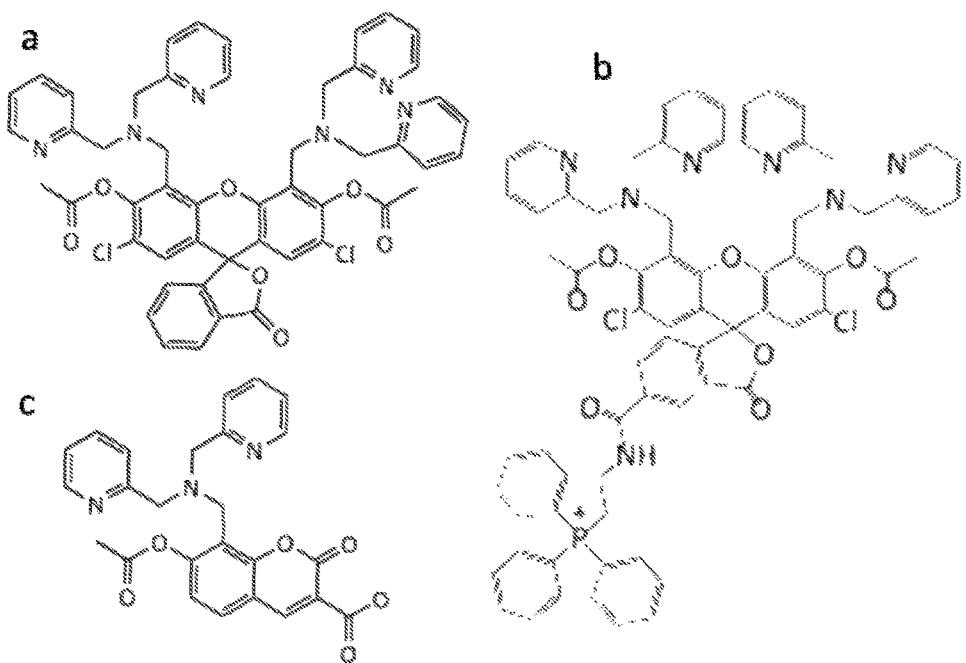
FIG. 1 depicts the structures of acetylated versions of (a) ZP1, (b) ZP1-TPP, and (c) 8-DPA-7-hydroxycoumarin-3-carboxylic acid.

Esterified pro-sensors were prepared by reacting a zinc sensor (e.g., ZP1) in acid anhydride (e.g., acetic anhydride) for >4 h at room temperature. The reaction was high yielding (>90% yield), and the resulting esterified sensor was purified by traditional chromatographic or recrystallization methods. This methodology was used to prepare acetylated (Ac) versions of ZP1, ZP1-triphenylphosphonium (ZP1-TPP), and 8-DPA-7-hydroxycoumarin-3-carboxylic acid (FIG. 1).

Figure 2:
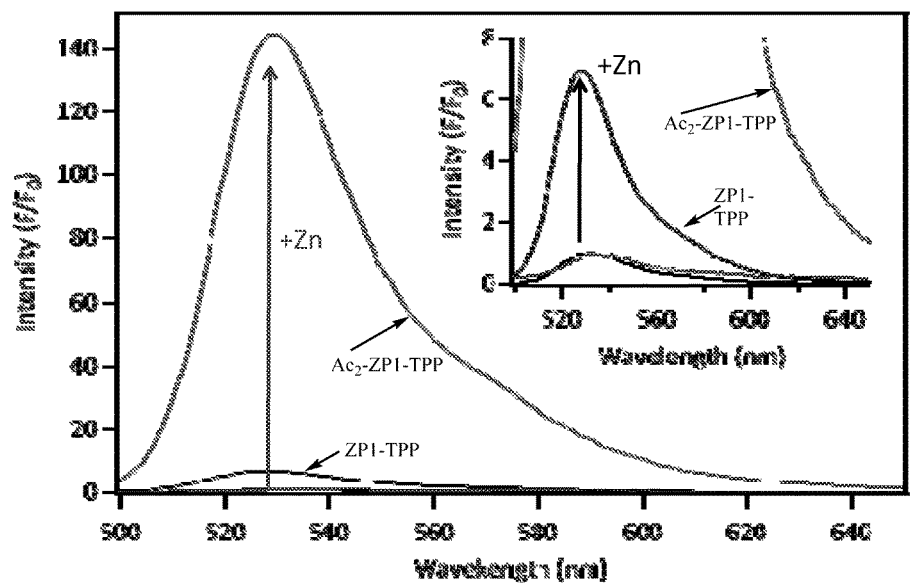
FIG. 2 depicts the normalized fluorescent spectra of DA-ZP1-TPP (also referred to as Ac$_2$-ZP1-TPP) and ZP1-TPP in the absence (dashed line) and presence (solid line) of excess ZnCl$_2$. Inset: The y-axis is magnified to aid in the visualization of the ~7-fold "turn-on" of ZP1-TPP.
Figure 3:
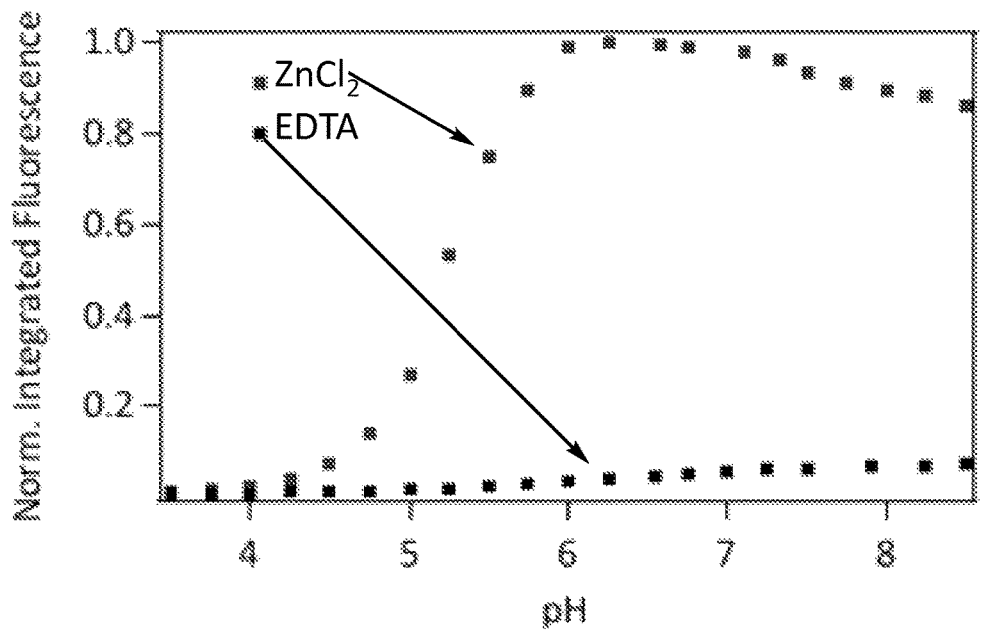
FIG. 3 depicts the pH profile of DA-ZP1-TPP in the presence of excess ZnCl$_2$ or ethylene diaminetetraacetic acid (EDTA).
Figure 4:
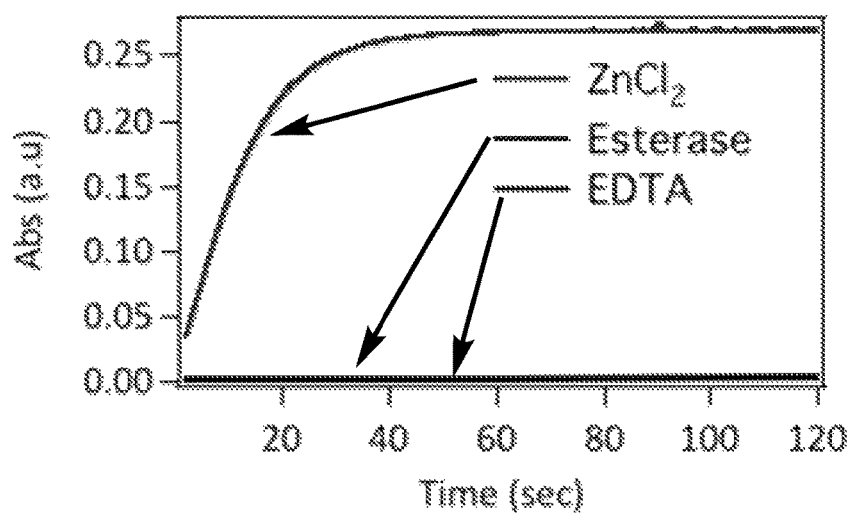
FIG. 4 depicts the time dependence of the hydrolysis of DA-ZP1-TPP by ZnCl$_2$, porcine liver esterase, or metal-free buffer (EDTA). The progress of each reaction was monitored by measuring the increase in absorbance of the ZP1 construct (510 nm (ZnCl$_2$) or 519 nm (EDTA and esterase)) as the DA-ZP1-TPP was hydrolyzed to ZP1-TPP.
Figure 5:
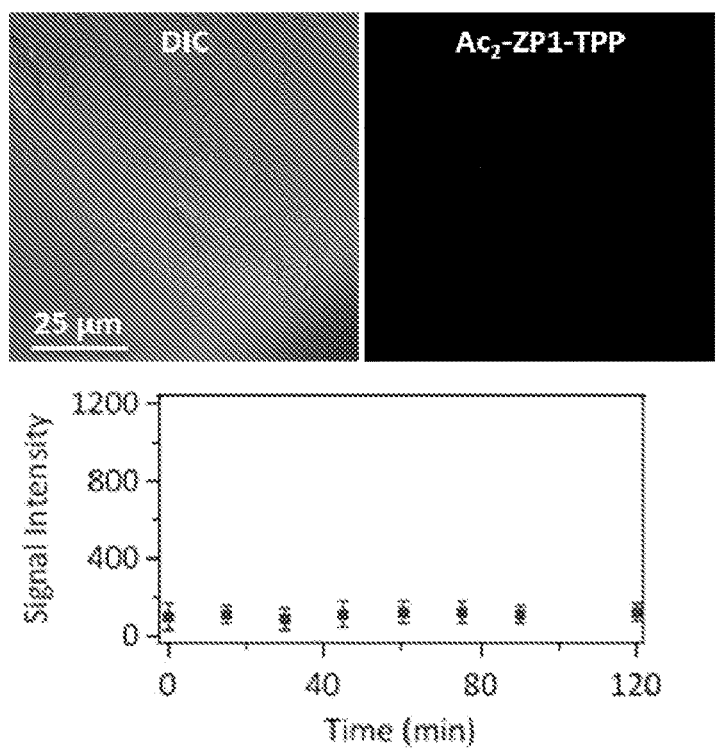
FIG. 5 depicts live cell imaging of HeLa cells that were bathed in a 1 μM solution of DA-ZP1-TPP in dye and serum free DMEM media for 30 min at 37° C. and 5% CO$_2$. The differential interference contrast (DIC) image shows the HeLa cells normal appearance and morphology. There was minimal fluorescent signal from DA-ZP1-TPP, consistent with the quenched fluorescent form of the sensor (top, right). The signal intensity was stable over 2 hours, suggesting the DA-ZP1-TPP is stable in cellulo.
Figure 6:
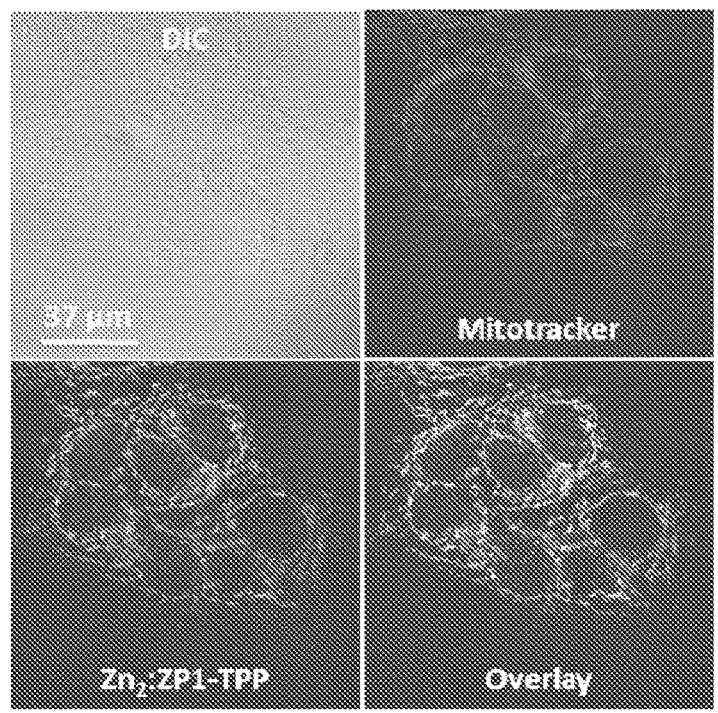
FIG. 6 depicts live cell imaging of HeLa cells. 500 nM mitotracker Red was bath-applied along with 1 μM DA-ZP1-TPP for 30 min at 37° C. and 5% CO$_2$. After exposure to 25 μM 1:2 zinc:pyrithione, fluorescent images were acquired and the co-localization of the two sensors was assessed. The calculated Pearson's correlation coefficient (r) was r=0.581±0.097 (n=9), which represents the average of 9 ROIs over three independent plates.
Figures 9, 10:
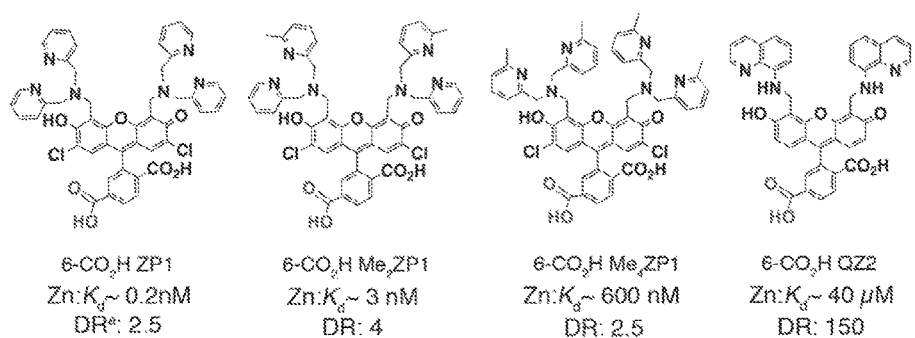
FIG. 9 tabulates photophysical, zinc-binding, and chemical properties of ZP1-TPP and DA-ZP1-TPP.
FIG. 10 depicts line drawings of representative 6-CO$_2$H ZP sensors that may be esterified. $^a$DR is the dynamic range, or the increase in brightness, that results from Zn(II) coordination.
Figure 11:
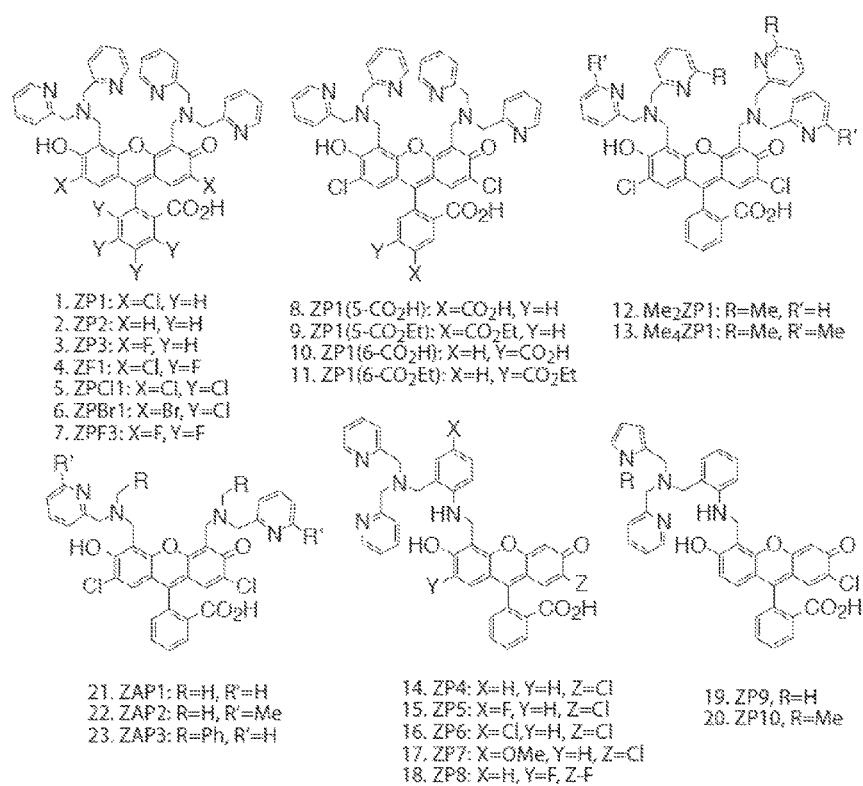
FIG. 11 depicts various fluorescein-based sensors that may be esterified.
Figure 12:
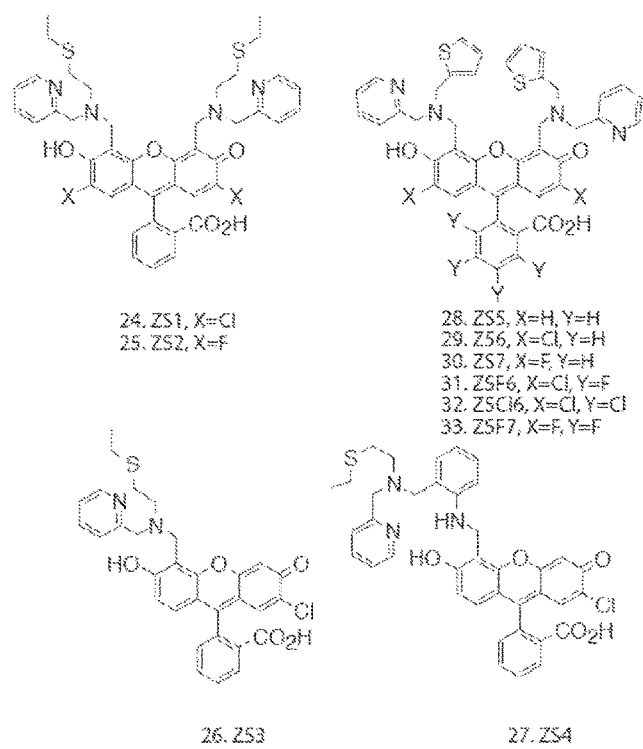
FIG. 12 depicts various fluorescein-based sensors that may be esterified.
Figure 13:
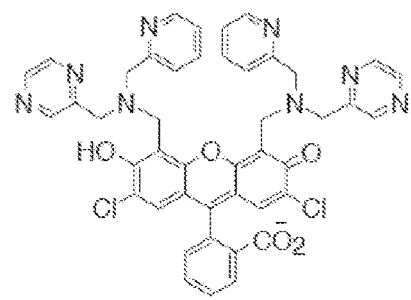
FIG. 13 depicts a fluorescein-based sensor that may be esterified.
Figure 14:
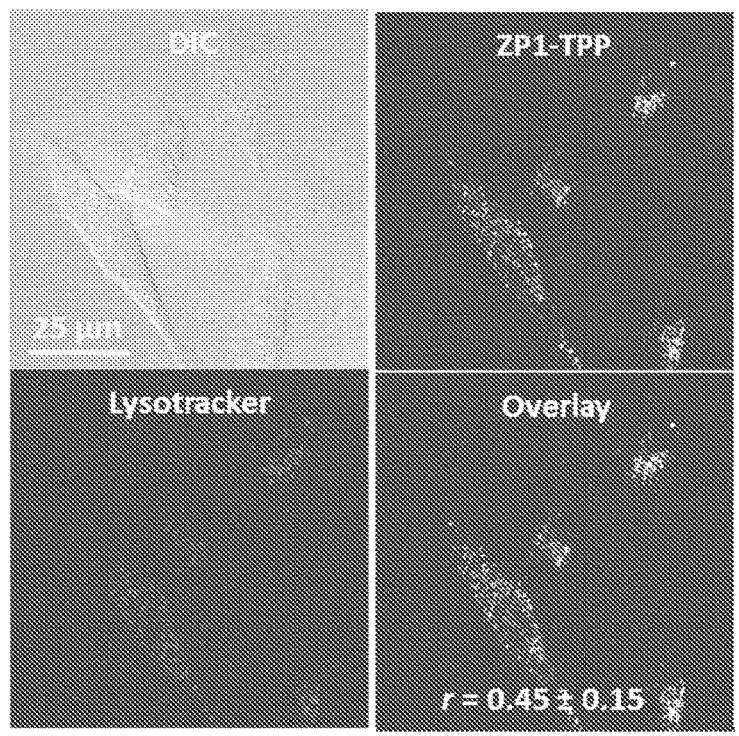
FIG. 14 depicts live cell imaging of HeLa cells. 1 μM Lysotracker Red was bath-applied along with 2 μM ZP1-TPP. The calculated Pearson's correlation coefficient (r) was r=0.45±0.15, which represents the average of 9 ROIs over three independent plates.
Figure 15:
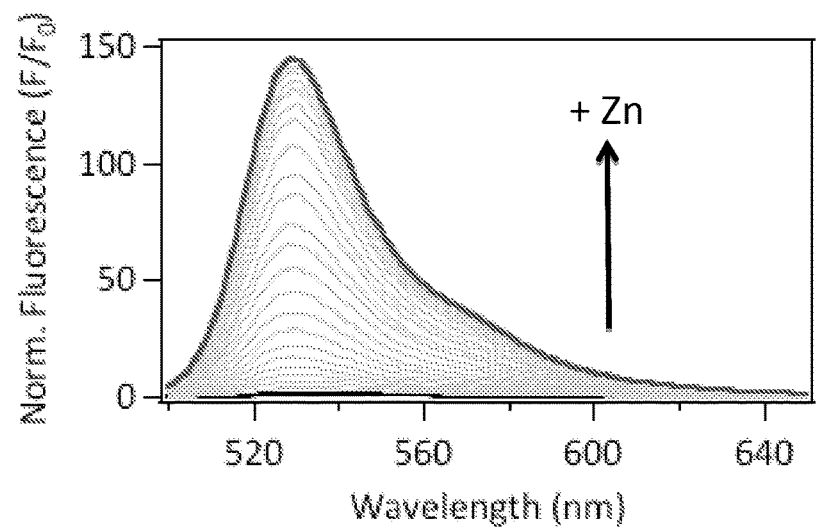
FIG. 15 depicts the observed change in the emission spectrum of DA-ZP1-TPP upon successive addition of increasing amounts of ZnCl$_2$, in 50 mM PIPES buffer (pH 7) and 100 mM KCl.

The inventive sensors have several important improvements over the current state of the art, including:
    A significantly improved dynamic range (FIG. 2 and FIG. 9), and pH profile (FIG. 3).
    Resistance to water and esterase-mediated hydrolysis both in vitro (FIG. 4) and in cellulo (FIG. 5).
    The ability to target subcellular organelles, such as the mitochondria (FIG. 6).

Figure 7:
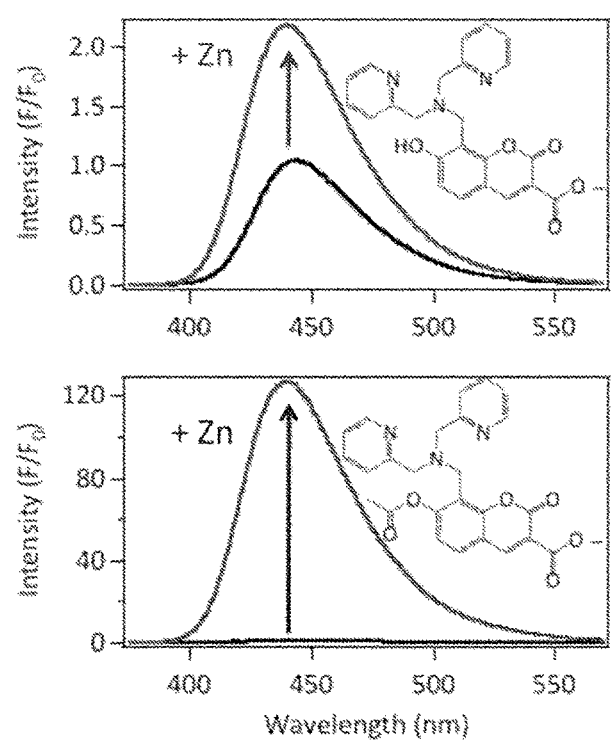
FIG. 7 depicts the zinc-induced fluorescence "turn-on" for the non-acetylated (top) and acetylated (bottom) versions of a zinc sensor based on 7-hydroxycoumarin-3-carboxylic acid. Spectra were acquired in 50 mM PIPES buffer (pH 7), 100 mM KCl with a $\lambda_{ex}$=360 nm.

Lastly, preliminary data (FIG. 7) and literature precedent suggest that this strategy will be generalizable to fluorophores that have phenolic oxygen atoms electronically participating in the fluorescence emission pathway. Examples of fluorophores that meet this criterion are coumarin, fluorescein, and resorufin derivatives.

Example 2

Kinetics of Zinc-Induced Turn-on

For $ZnCl_2$-2.75 μM DA-ZP1-TPP was incubated at 37° C. in 50 mM PIPES buffer (pH 7) and 100 mM KCl. 5 μL of 50 mM $ZnCl_2$ were added (125 μM final concentration) and the absorbance at 510 nm was measured continuously (0.3 s averaging time) for 2 min. $k_{obs}=8.55\times10^{-2}\pm1.9\times10^{-2}$ ($s^{-1}$); $t_{1/2}=8.10$ s.

Example 3

Acylated Peptide-Based Sensor

Figure 16:
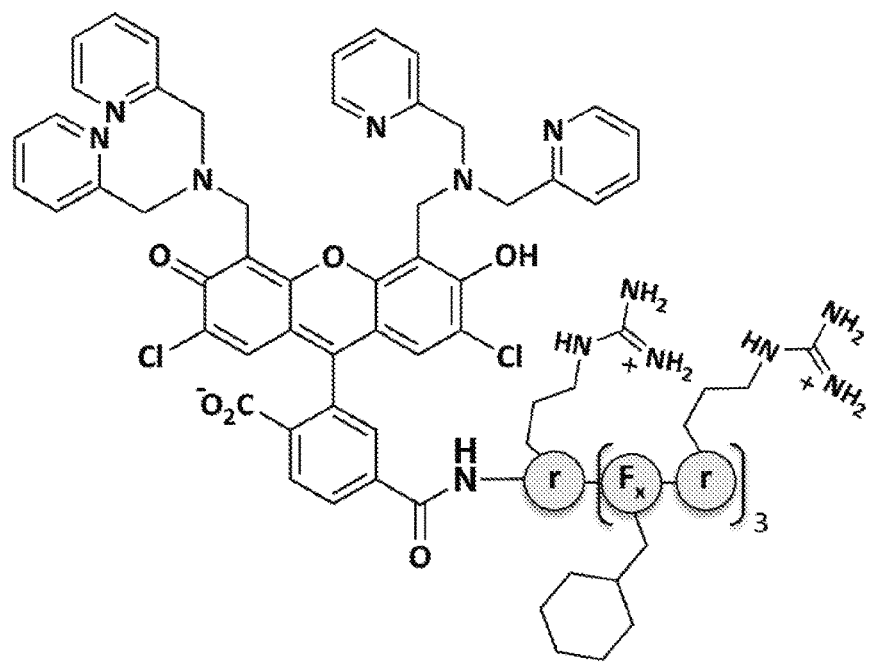
FIG. 16 depicts the structure of a peptide-based sensor (ZP1-r(F$_x$r)$_3$) that may be esterified to give DA-ZP1-r(F$_x$r)$_3$ (also referred to as Ac$_2$-ZP1-r(F$_x$r)$_3$). The arginine residues have the D configuration, while the F$_x$ residues have the L configuration.

FIG. 16 depicts a peptide-based sensor ($ZP1-r(F_xr)_3$) that was esterified into a compound of the invention.

DA-ZP1-r(F$_x$r)$_3$ was prepared by adding 400 μL of a 2.6 mM stock solution of the peptide in DMSO to 3 mL of acetic anhydride. The solution was mixed at RT for 6 hrs, diluted with water, and lyophilized. The resulting residue was purified by RP-HPLC, using standard procedures. The resulting peptide was >99% pure based on absorbance values at 220 nm and 280 nm.

Figure 17:
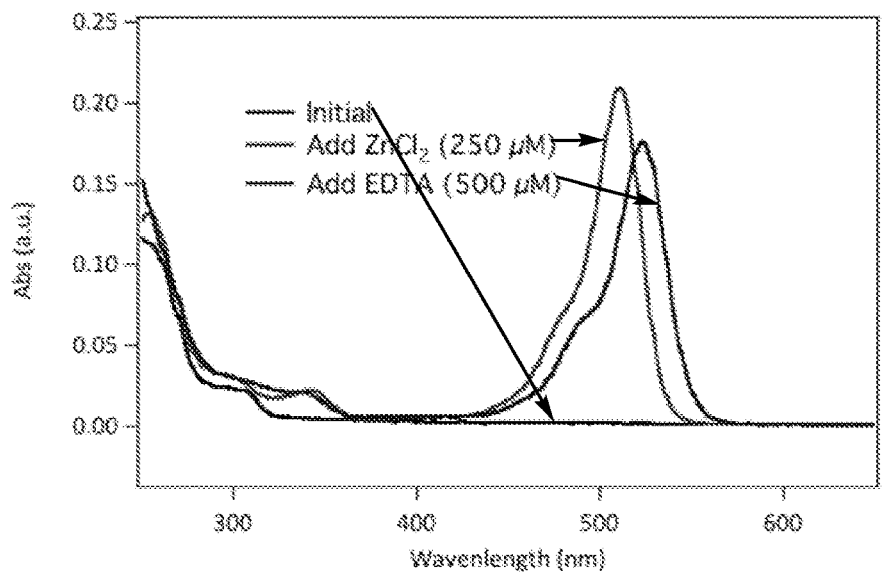
FIG. 17 depicts the change in absorbance of DA-ZP1-r(F$_x$r)$_3$ upon addition of zinc and EDTA.
Figure 18:
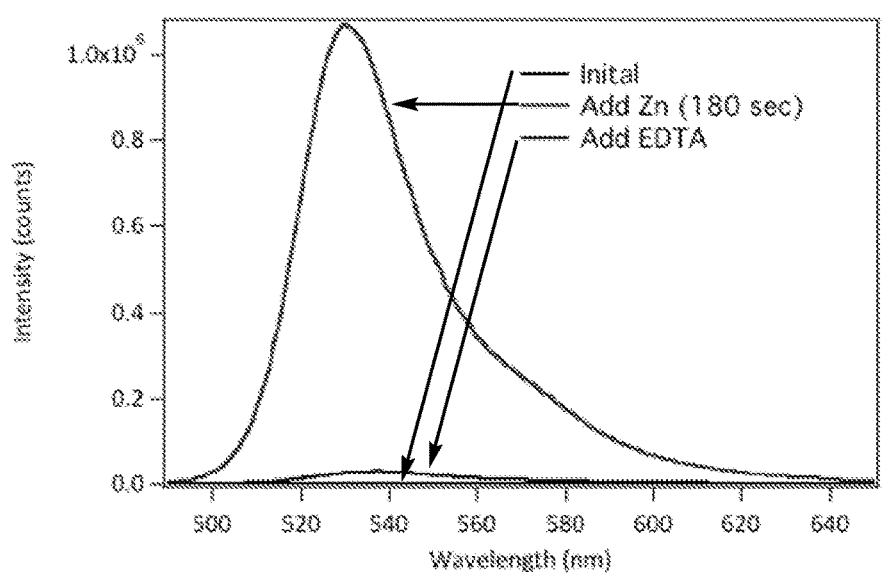
FIG. 18 depicts the fluorescence intensity of DA-ZP1-r(F$_x$r)$_3$ upon addition of zinc and EDTA.

Spectra were acquired in 50 mM PIPES (pH 7) with 100 mM KCl. For this titration, a single excitation wavelength of $\lambda_{ex}$=485 nm was used. See FIGS. 17 and 18.

Figure 19:
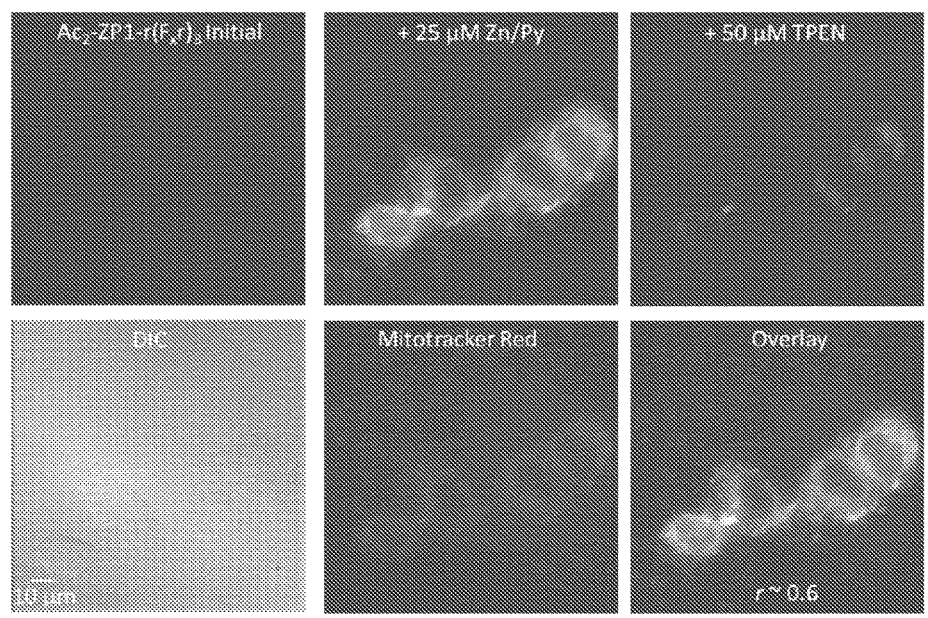
FIG. 19 depicts live cell imaging of HeLa cells in the presence of DA-ZP1-r(F$_x$r)$_3$.

FIG. 19 depicts HeLa cells subjected to the following conditions: 7 μM DA-ZP1-r(F$_x$r)$_3$, 250 nM MitoTracker Red, 1 h.

Example 4

ZP1-TPP is Sequestered in Endo/Lysosomes and Unable to Respond to Mobile Zinc In targeting mitochondria, we relied on an aminoethyl derivative of triphenylphosphine to generate the lipophilic aminoethyltriphenylphosphonium (TPP) cation. TPP delivers payloads, including fluorescent sensors, to the mitochondrial matrix by exploiting the negative potential maintained by actively respiring mitochondria. The free amino group on the aminoethyl TPP derivative provided a convenient synthetic handle for attachment of 6-CO$_2$H ZP1. The resulting construct, ZP1-TPP, has photophysical and zinc-binding properties similar to those of other ZP1 derivatives, yielding an ~7-fold zinc-induced fluorescence response with an apparent $K_{d-Zn}$ of 0.60 (±3) nM in cuvette studies. Live cell imaging of ZP1-TPP in HeLa, however, revealed a distinctive punctate pattern that did not respond significantly to changing intracellular zinc levels. Fluorescence imaging studies of HeLa cells pretreated with ZP1-TPP and organelle-specific dyes revealed that ZP1-TPP colocalizes moderately with LysoTracker Red (Pearson's r=0.45±0.15), but not at all with MitoTracker Red (r=−0.15±0.07). Moreover, owing to the pH sensitivity of ZP1, when present in the acidic compartments of endo/lysosomes the sensor is protonated, which severely diminishes the ability of ZP1-TPP to respond to mobile zinc ions.

Example 5

Assessing the Physical Requirements for TPP-Mediated Targeting of Fluorophores to Mitochondria To understand better the limitations of TPP in directing fluorophores to mitochondria, we prepared two additional TPP-derivatives, one based on 6-carboxyfluorescein (FL-TPP) and one on coumarin 343 (C343-TPP). Because positive charge and hydrophobicity are the main design criteria for directing molecules to respiring mitochondria, we postulated that, at pH 7.4, deprotonation of the tertiary amine on a DPA arm of ZP1-TPP (pK$_a$=6.96) coupled with the presence of the anionic 2-carboxylate were primarily responsible for the inability of ZP1-TPP to target mitochondria. To test this hypothesis, we conducted live cell fluorescence imaging experiments with FL-TPP. Without the appended DPA arms, FL-TPP is predominantly anionic at physiological pH (phenolic oxygen pK$_a$=6.7). Not only did FL-TPP fail to accumulate in mitochondria, it was cell-impermeable under our imaging conditions. In contrast, the cationic C343-TPP strongly colocalized with MitoTracker Red in live HeLa cells (Pearson's r=0.72±0.02). To quantify the effect of hydrophobicity in mitochondrial-targeting, we measured the octanol/aqueous buffer partition coefficient (log P) for our TPP constructs and two MitoTracker dyes. We then tabulated the log P, charge of the predominate species in solution at physiological pH, and cellular localization for each dye (Table 1). From these data we concluded that TPP alone is not sufficient to ensure mitochondrial targeting. Along with cationic charge, a minimum level of lipophilicity must be reached in order to evade endo/lysosomal sequestration and enable effective mitochondrial targeting.

TABLE 1

Lipophilicity, charge of predominate species in solution at physiological pH, and observed cellular localization of various dyes in live HeLa cells.

| Compound | log P[a] | Charge[b] | Localization[c] |
|---|---|---|---|
| Mitotracker Red | 1.15 ± 0.04 | +1 | Mitochondria |
| DA-ZP1-TPP | 0.74 ± 0.18 | +1 | Mitochondria |
| C343-TPP | 0.72 ± 0.05 | +1 | Mitochondria |
| Mitotracker Green | 0.56 ± 0.02 | +1 | Mitochondria |
| ZP1-TPP | −0.11 ± 0.01 | Zwitterion | Endo/lysosome |
| FL-TPP | −0.39 ± 0.03 | −1 | Extracellular |

[a]Log P values were measured in octanol/water, buffered at pH 7 with 10 mM Tris, using a modified shake-flask procedure.
[b]Charge of the predominate species in solution at physiological pH = 7.4.
[c]Observed localization in fluorescence microscopy studies in live HeLa cells. Localization for ZP1 in live Cos-7 cells was previously reported.

Example 6

Design, Synthesis, and Evaluation of DA-ZP1-TPP, a Zinc-Reaction-Based Probe that Targets Mitochondria To create a ZP1-TPP derivative optimized for mitochondrial localization, we developed a novel reaction-based probe based on fluorescein diacetate. Modifying the fluorescein scaffold with esters or ether derivatives is a common strategy to increase cell permeability, retention, and sensitivity of fluorescein-based probes. In traditional applications, acetyl or acetoxymethyl groups are added to the phenolic oxygen atoms of the xanthene ring structure resulting in formation of the non-fluorescent lactone conformation. These modifications neutralize the negative charge from the fluorescein carboxylate, increase the overall hydrophobicity of the probe, and allow the fluorophore readily to cross the plasma membrane. Once in the cytoplasm, intracellular hydrolases typically restore the fluorescence properties of the sensors by hydrolyzing the ester functionality appended to the fluorophore. This approach relies on endogenous enzymes, the cellular expression of which can be organelle- and cell-type dependent. In contrast, our approach uses zinc ions to promote cleavage of the acetyl moieties, attenuate PeT quenching from the DPA arms, and restore fluorescence (FIG. 8).

Figure 20:
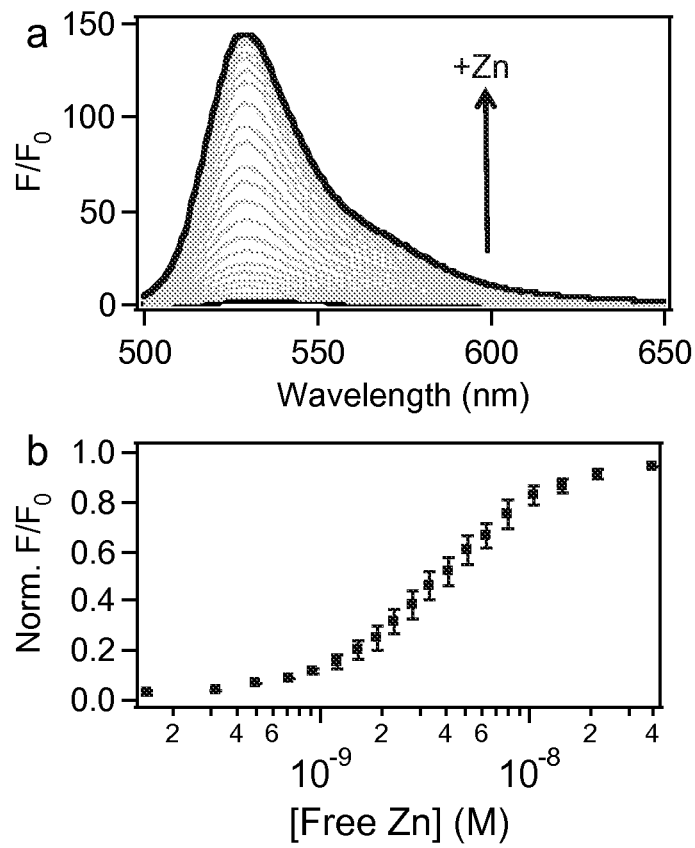
FIG. 20 depicts Zn(II)-dependent fluorescence signal enhancement of DA-ZP1-TPP. (a) Normalized fluorescence spectra of a 1 µM solution of DA-ZP1-TPP, in 50 mM PIPES buffer (pH 7) with 1 mM EDTA, 2 mM $CaCl_2$, and 100 mM KCl, upon increasing concentrations of free zinc ions. (b) Zinc binding isotherm for the data in (a), normalized to the fluorescence signal under zinc saturating conditions ($\lambda_{ex}$=495 nm).

The diacetylated version of ZP1-TPP, designated DA-ZP1-TPP, was readily prepared by reacting ZP1-TPP with acetic anhydride overnight at room temperature. Over the course of the reaction, the mixture turned from a dark, salmon-colored solution to a light, nearly colorless liquid, which was purified by HPLC. Consistent with the sensor adopting the lactone conformation, DA-ZP1-TPP is optically silent at $\lambda_{abs}$>350 nm and essentially non-fluorescent (Φ≤0.001). Addition of nanomolar concentrations of zinc ions results in a large increase in both the absorption $\lambda_{abs-Zn}$=510 nm) and fluorescence ($\lambda_{em-Zn}$=529 nm, FIG. 20a) spectral bands of DA-ZP1-TPP. These optical changes combine to yield a >140-fold increase in the fluorescence signal ($\Phi_{Zn}$=0.75±0.03, FIG. 20). Analysis of the reaction products by analytical HPLC and ESI-MS confirm that DA-ZP1-TPP is transformed back to ZP1-TPP in the presence of Zn(II). Whether the mode of zinc-mediated ester hydrolysis proceeds by internal or external hydroxide attack remains to be determined. Notably, DA-ZP1-TPP retains a measure of reversibility, differentiating it from most reaction-based probes. Addition of a chelator (EDTA) attenuates the fluorescence signal ~5-fold ($\Phi$=0.15±0.02) in the cuvette (FIG. 22) with a concomitant redshift in the absorption spectrum ($\lambda_{abs}$=522 nm). Reversibility of the fluorescence signal is an important feature for zinc-responsive probes, because it allows confirmation that the observed increase in fluorescence signal is due to Zn(II) and not the result of an artifact. By employing ZP1 as the sensor scaffold, DA-ZP1-TPP retains the quenching ability of the DPA metal-binding arms, which affords a minimally fluorescent metal-free state even after hydrolysis of the acetyl groups. Although it cannot reverse completely, DA-ZP1-TPP is a rare example of reaction-based probe that has even partial reversibility.

Example 7

DA-ZP1-TPP has a Significantly Improved pH Profile

Figure 21:
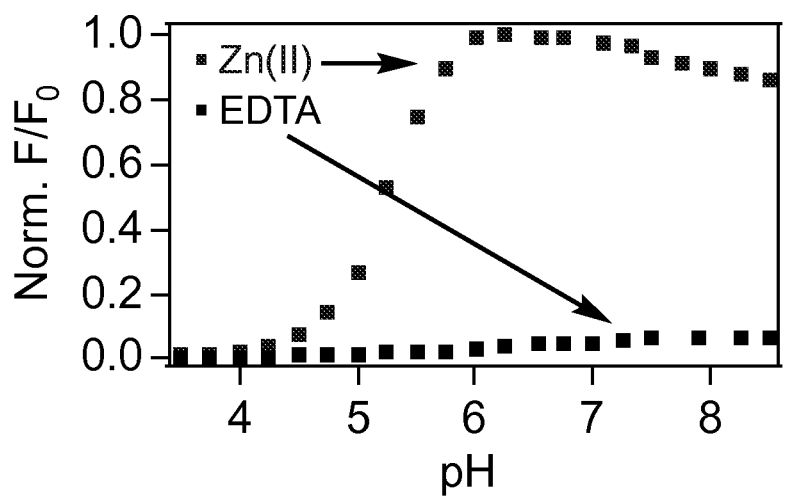
FIG. 21 depicts normalized fluorescence signals for DA-ZP1-TPP as a function of increasing pH in the presence of 125 µM $ZnCl_2$ or 250 µM EDTA. Data were acquired 17.5 mM (0.1% v/v) acetic acid in milli-Q $H_2O$ beginning at pH 3.5. The pH of the solution was increased by sequential addition of aqueous KOH. The total volume of KOH added was less than 5% of the total volume. $\lambda_{ex}$=475 nm.

Next, we investigated the pH profile of DA-ZP1-TPP. The use of nitrogen atoms to coordinate zinc endows Zinpyr sensors with selectivity for zinc over calcium and magnesium, but also renders them pH sensitive. The p$K_a$ of the tertiary nitrogen atoms on the DPA units of ZP1 are 6.96 and 8.12, respectively. Protonation of these amines leads to increased background fluorescence because protons can diminish PeT in a manner similar to that of zinc ions. In contrast to previous Zinpyr sensors, DA-ZP1-TPP displays no significant fluorescence turn-on under acidic conditions in the absence of zinc (FIG. 21). In the presence of excess zinc ions, however, the sensor displays a strong zinc-dependent fluorescence response at pH>5. The lack of response from DA-ZP1-TPP under acidic conditions is a significant improvement over any of the current members of the Zinpyr family. We anticipate that reaction-based zinc sensors will greatly improve our ability to image mobile zinc in acidic vesicles and compartments.

Example 8

DA-ZP1-TPP Yields a Zinc-Induced Fluorescence Response

Figure 22:
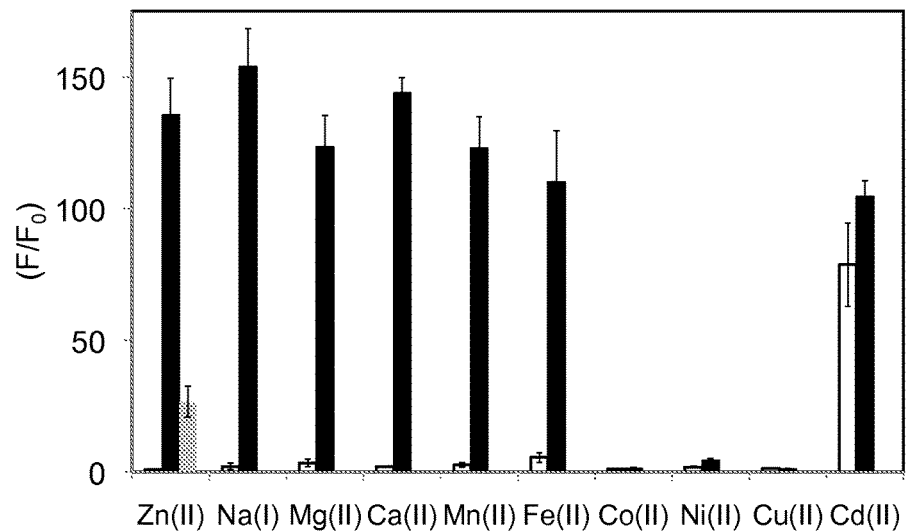
FIG. 22 depicts metal ion selectivity of DA-ZP1-TPP. Average normalized fluorescence intensities for a 1.1 µM solution of DA-ZP1-TPP in 50 mM PIPES buffer (pH 7) with 100 mM KCl at 25° C., after addition of 50 µM-2 mM concentrations of various metal ions (white bars), followed by addition of 50 µM $ZnCl_2$ (black bars). The grey column represents the average sensor intensity after addition of 100 µM EDTA. Data were normalized to initial measured emission intensity at $\lambda_{ex}$=495 nm.
Figure 23:
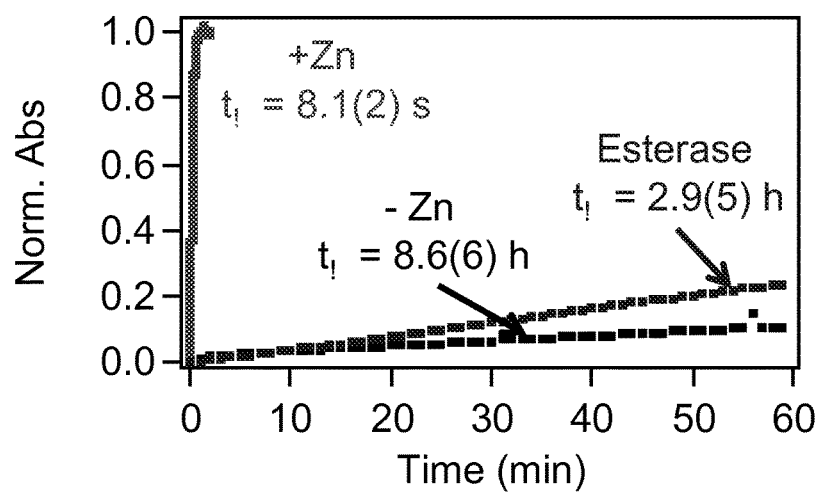
FIG. 23 depicts kinetic traces for the deacetylation of DA-ZP1-TPP. The half-life for deacetylation of a 2.75 µM solution of DA-ZP1-TPP, at 37° C. in 50 mM PIPES buffer (pH 7) and 100 mM KCl, was measured in the presence of 125 µM $ZnCl_2$ (+Zn), 250 µM EDTA (−Zn), or 1.25 units of porcine liver esterase (Esterase). The change in absorbance at 520 nm (EDTA and esterase) or 510 nm ($ZnCl_2$) was used to monitor the reaction.
Figure 25:
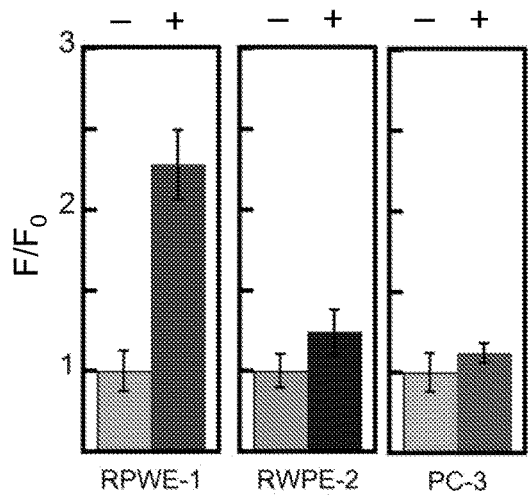
FIG. 25 depicts decreased mitochondrial zinc uptake in cancerous cell lines. RWPE-1, RWPE-2, and PC-3 prostate cell lines were incubated for 24 h in medium supplemented with (+) and without (−) 50 µM $ZnCl_2$. RWPE-1 is the only cell line that has a statistically significant (p<0.001) increase in mitochondrial zinc uptake when incubated in zinc-enriched media.

DA-ZP1-TPP has a zinc-induced fluorescence response and is relatively stable to uncatalyzed hydrolysis and esterase activity. Analogous to ZP1, DA-ZP1-TPP responds to Zn(II) over biologically relevant cations such as Ca(II) and Mg(II) (FIG. 22). Other late 3d-block transition metal ions, such as Co(II) and Cu(II), can coordinate to DA-ZP1-TPP but are generally not available in appreciable chelatable quantities within the cell. In addition to monitoring selectivity in the fluorescence response, we used UV-vis spectroscopy to investigate the rate and zinc-specificity of metal-mediated ester hydrolysis. DA-ZP1-TPP deacetylation results in opening of the lactone ring and restoration of conjugation across the xanthene ring. By monitoring the absorbance of the xanthene it system, we could interrogate deacetylation kinetics in a manner that is independent of the fluorescence response. Under pseudo-first-order conditions in 50 mM PIPES buffer (pH 7) with 100 mM KCl at 37° C., addition of ZnCl$_2$ resulted in a zinc-induced increase in absorbance at $\lambda_{max}$=510 nm. The kinetic trace for this process fits well to a single exponential function with $t_{1/2-Zn}$=8.1 s (FIG. 23). Under analogous conditions, but in the presence of 250 µM EDTA or 1.25 units of porcine liver esterase instead of zinc, the rate of deacetylation for DA-ZP1-TPP is dramatically slower, with $t_{1/2-EDTA}$ of 8.6 h and $t_{1/2-Esterase}$ of 2.9 h, respectively (FIG. 25). Notably, both Cu(II) and Co(II) can mediate ester hydrolysis. These observations are consistent with the reported hydrolytic ability of both metal ions in small-molecule biomimetic and sensing systems. Co(II)-mediated ester hydrolysis was fit to a single exponential function with $t_{1/2-Co(II)}$=3.04 s, whereas Cu(II) had significantly slower kinetics that required two sequential irreversible steps for a good fit. The calculated half-lives for the two irreversible steps are $t_{1/2}$=6.08 min and $t_{1/2}$=39.5 min, respectively. As shown in FIG. 22, however, cross-reactivity with Co(II) and Cu(II) would quench the fluorescence signal and thus would not lead to any false fluorescence response. To determine whether ester hydrolysis depends on the metal-binding core of DA-ZP1-TPP, we measured the deacetylation kinetics of fluorescein diacetate (DA-FL) under analogous conditions. As predicted, DA-FL responds rapidly to esterase, but is relatively stable to hydrolysis and zinc-mediated deacetylation. The prolonged stability of DA-ZP1-TPP with respect to hydrolytic and enzymatic deacetylation in the absence of zinc ions, coupled with the rapid zinc-induced fluorescence response of the pro-sensor, indicate that DA-ZP1-TPP can serve as an effective cellular imaging agent for mobile zinc.

Example 9

Figure 24:
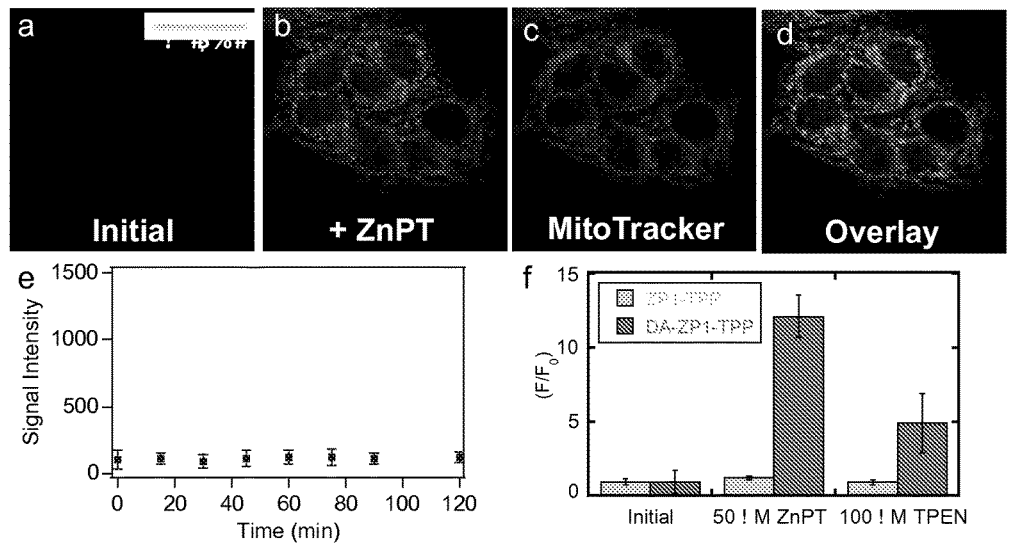
FIG. 24 depicts fluorescence images of live HeLa cells. HeLa cells were pretreated with a 1 µM solution of DA-ZP1-TPP in dye- and serum-free medium for 30 min (37° C., 5% $CO_2$). Initial images (a) showed minimal fluorescence signal that was stable for a period of 2 h (e). Addition of 50 µM ZnPT (b) resulted in an ~12-fold increase in intensity, which was sensitive to TPEN (f, right bars). This result is in contrast to the nonacetylated sensor, which is insensitive to ZnPT (f, left bars). The signal from MitoTracker Red (c) correlates well with the signal from the zinc-bound sensor (d). Pearson's r=0.64±0.1 (n=18).

DA-ZP1-TPP is Stable to Intracellular Hydrolases, Targets Mitochondria, and Responds to Chances in Intracellular Zinc Levels We used HeLa cells as a model system to evaluate the ability of DA-ZP1-TPP to target mitochondria and respond to changes in intracellular zinc levels. Live HeLa cells were pretreated with medium containing 1 µM DA-ZP1-TPP and 250 nM MitoTracker Red for 30 min (37° C., 5% CO$_2$) prior to imaging (FIG. 24). Initial images showed minimal fluorescence intensity from the construct (FIG. 24a), consistent with the low endogenous levels of mobile zinc in HeLa cells. Over a two-hour period, the fluorescence intensity from the sensor remained constant, implying that the acetylated form is stable against intracellular esterases (FIG. 24e). Addition of 50 µM Zn/pyrithione (ZnPT) resulted in an ~12.1-fold increase in fluorescence intensity that visually overlapped with the signal from MitoTracker Red (FIG. 24). Quantitative analysis of the fluorescence signals obtained from MitoTracker Red and zinc-bound ZP1-TPP revealed that the two dyes strongly co-localized, with Pearson's r=0.64±0.1. Addition of 100 µM TPEN attenuated the fluorescence signal by ~2.4-fold (FIG. 24f). On the basis of these fluorescence microscopy studies with HeLa cells we conclude that (i) in contrast to the nonacetylated form of the sensor (vide supra), DA-ZP1-TPP has sufficient cationic character and hydrophobicity (Log P=0.74±0.18, Table 1) to target mitochondria effectively; (ii) DA-ZP1-TPP is stable against intracellular hydrolysis over a period of ≥2 h; and, (iii) DA-ZP1-TPP responds to changes in intracellular mobile zinc levels, an observation that is corroborated by sensor shut-off upon addition of a chelator. Together these data strongly support acetylation of fluorescein-based zinc sensors as an effective strategy both to improve the dynamic range of fluorescein-based zinc sensors and to facilitate cellular targeting by a localization vector. We anticipate that this strategy will be applicable to related families of fluorophores.

Example 10

Investigating Zinc Trafficking to Mitochondria in Prostate Cells

With a new mitochondrial-targeting sensor in hand, we used DA-ZP1-TPP to investigate the ability of prostate cell lines to accumulate zinc within their mitochondria. RWPE-1 and RWPE-2 are a pair of genetically similar cell lines that retain normal epithelial cell morphology, express cytokeratin markers for prostate epithelial cells, and are hormone sensitive. RWPE-2 cells, however, are tumorigenic and accumulate less zinc owing to a decrease in ZIP1 expression and altered cellular localization of ZIP3. To explore the ability of RWPE-1 and -2 cells to sequester zinc in mitochondria, we measured the fluorescence intensity of DA-ZP1-TPP in both lines after the cells were bathed in normal or zinc-enriched (50 μM $ZnCl_2$) keratinocyte serum-free medium (KSFM) for 24 h prior to imaging. RWPE-1 cells bathed in zinc-enriched medium have a fluorescence signal intensity that is ~2.3-fold higher than cells bathed in normal medium (FIG. 25). This result is consistent with the ability of healthy epithelial prostate cells to accumulate high concentrations of total zinc, but it also reveals that the observed changes correlate with increased mobile zinc within mitochondria. In contrast, RWPE-2 cells showed no statistically significant increase in fluorescence signal under analogous conditions (FIG. 25). Importantly, in both cell lines the observed fluorescence signals from DA-ZP1-TPP are sensitive to ZnPT and TPEN and have good correlation with MitoTracker Red, the Pearson's r values being 0.68±0.09 and 0.59±0.1 for RWPE-1 and -2, respectively. To further corroborate these observations, we conducted an analogous experiment in PC-3 cells, a model cell line for human prostatic adenocarcinoma metastatic to bone. Consistent with the results from the RWPE cell line, PC-3 cells showed no statistically significant increase in sensor fluorescence intensity when bathed in zinc-enriched (50 μM $ZnCl_2$) RPMI 1640 medium with 10% FBS for 24 h prior to imaging (FIG. 25). To account for the zinc-binding ability of FBS, we repeated the imaging experiments with PC-3 cells in serum-free RPMI 1640 medium supplemented with 15 μM $ZnCl_2$ for 3 h. Under these conditions, no statistically significant increase in fluorescence intensity was observed. Our fluorescence imaging results from the RWPE and PC-3 cell lines are in agreement with the results of studies using homogenized prostatic tissue, which assert a correlation between altered zinc trafficking and prostate cancer. However, our data are the first, to our knowledge, that demonstrate the inability of tumorigenic prostate cells to accumulate mobile zinc within their mitochondria. The fact that the RWPE-1, -2 and PC-3 cell lines all accumulate increased levels of total zinc when bathed in zinc-enriched medium, and the lack of a defined mitochondrial ZnT raise questions about the mechanism of mobile zinc accumulation within mitochondria of healthy epithelial cells. One possible explanation is differential expression of metallothionein isoforms in cancerous cell lines. Another possibility is altered zinc trafficking pathways resulting from modified signaling cascades and transcription factor activity. Addressing these and other possible explanation will require a detailed molecular understanding of the action of mobile zinc within healthy and tumorigenic prostate cells. In combination with biochemical investigations, the ability to direct zinc-responsive fluorescent probes to discrete cellular locales should provide valuable insight for understanding the function of mobile zinc within the prostate.

Example 11

Synthesis of Peptides with N-Terminal Reaction-Based Probes

To establish the compatibility of (DA-ZP1) with solid-phase peptide synthesis (SPPS), we created a three-residue, all alanine model peptide. Starting from Rink amide resin, Fmoc-protected alanine residues were sequentially added using standard procedures. The (6-$CO_2$H) ZP1 fluorophore was introduced onto the N-terminus of the peptide by developed methodology. The resin was split into two portions; one portion was cleaved and purified by HPLC yielding the peptide ZP1-$A_3$. The second portion was allowed to react with a solution of acetic anhydride (50%, v/v) in dimethylformamide (DMF) for 5 h. The resin was then washed with DMF and dichloromethane, dried, and cleaved in mixture of triisopropylsilane (5%, v/v) in trifluoroacetic acid. The overall yield for the synthesis of DA-ZP1-$A_3$ was estimated to be 44% by analytical HPLC.

As a parallel strategy, acetyl groups were installed onto ZP1-peptide derivatives by stirring the purified ZP1-labelled peptide in a mixture of acetic anhydride in dimethyl sulfoxide (DMSO) at room temperature for ≥4 h (see Supplementary Information for details). Under our reaction conditions, moderate to excellent yields (52-98%) were obtained. Using these synthetic routes, we synthesized DA-ZP1-$R_9$, DA-ZP1-r($F_x$r)$_3$, DA-DCF-r($F_x$r)$_3$, as well as their non-acetylated analogues. When acetylating unprotected peptides in solution, the use of 4-dimethylaminopyridine (DMAP) resulted in non-specific modification of peptide sidechains (data not shown). The successful synthesis and purification of these constructs demonstrates that our reaction-based probes are compatible with the cleavage and purification conditions of SPPS and that zinc-reactive acetyl groups can be incorporated onto ZP1-labelled peptides with moderate to excellent yields.

Example 12

Figure 26:
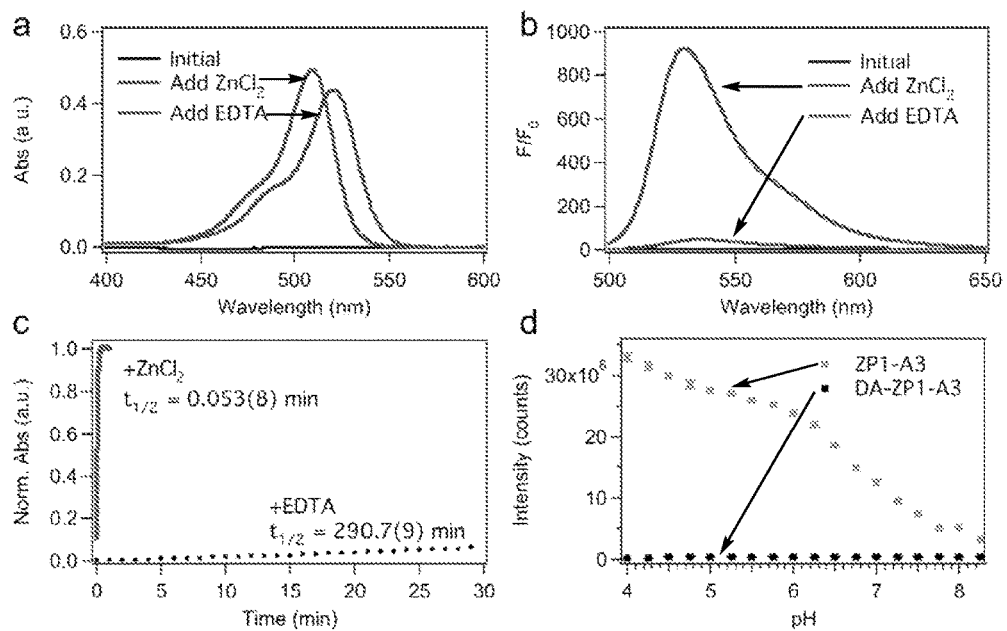
FIG. 26 depicts in vitro characterization of DA-ZP1-$A_3$. (a) UV-vis and (b) fluorescence spectra of a 5 µM solution of DA-ZP1-$A_3$ in buffer (50 mM PIPES, 100 mM KCl; pH 7). Spectra were acquired initially, upon addition of 100 µM $ZnCl_2$, and again after addition of 200 µM EDTA. (c) Time-dependent change in the normalized absorbance of a ca. 5 µM solution DA-ZP1-$A_3$ at 37° C. in buffer (50 mM PIPES, 100 mM KCl; pH 7) in the presence of 100 µM $ZnCl_2$ ($\lambda_{abs}$=510 nm) or EDTA ($\lambda_{abs}$=520 nm). (d) Integrated fluorescence intensity of a 1 µM solution of ZP1-$A_3$ (circles) or DA-ZP1-$A_3$ (squares) as a function of pH.

DA-ZP1-Peptides have Large Dynamic Ranges, are Selective for Zn(II), and pH Insensitive Using DA-ZP1-$A_3$ as a model system, we assessed its photophysical and zinc-binding properties (FIG. 26). DA-ZP1-$A_3$ is spectroscopically silent at $\lambda_{abs}$>350 nm and essentially non-fluorescent (Φ<0.001). Addition of excess $ZnCl_2$ rapidly restores ($t_{1/2}$=0.053±0.008 min) the absorption ($\lambda_{abs,\ Zn}$=509 nm) and emission ($\lambda_{em,\ Zn}$=530 nm; ($\Phi_{Zn}$=0.80±0.03) bands associated with 2',7'-dichlorofluorescein. Removing zinc ions from the sensor with ethylenediaminetetraacetic acid (EDTA) yields ZP1-$A_3$, which has photophysical and zinc-binding properties similar to those of other Zinpyr sensors ($\lambda_{abs}$=519 nm; $\lambda_{em}$=538 nm; ($\Phi_{Zn}$=0.14±0.01; $K_{d-Zn}$=0.38±0.04 nM). Spectroscopic and zinc-binding properties of all constructs were in accord with expectations, and we note a small redshift in the absorption and emission maxima when the sensor is attached to the $R_9$ and r($F_x$r)$_3$ peptides.

In contrast to the non-acetylated ZP1-A$_3$, DA-ZP1-A$_3$ does not show any significant turn-on under acidic conditions (FIG. 27d). Traditional Zinpyr sensors rely solely on photoinduced electron transfer (PET) from nitrogen-rich zinc-binding units to quench the metal-free form of the probe.[10b] Nitrogen donors provide selectivity for zinc over biologically abundant metal ions, such as calcium and magnesium, but they also render Zinpyr sensors pH sensitive. By forcing the fluorescein scaffold into the non-fluorescent lactone isomer, the zinc-reactive acetyl groups introduce an additional quenching mechanism and alleviate unwanted proton induced turn-on.

Example 13

Peptide Vectors Target ZP1 to the Cytoplasm/Nucleus, Vesicles, or Mitochondria

Figure 27:
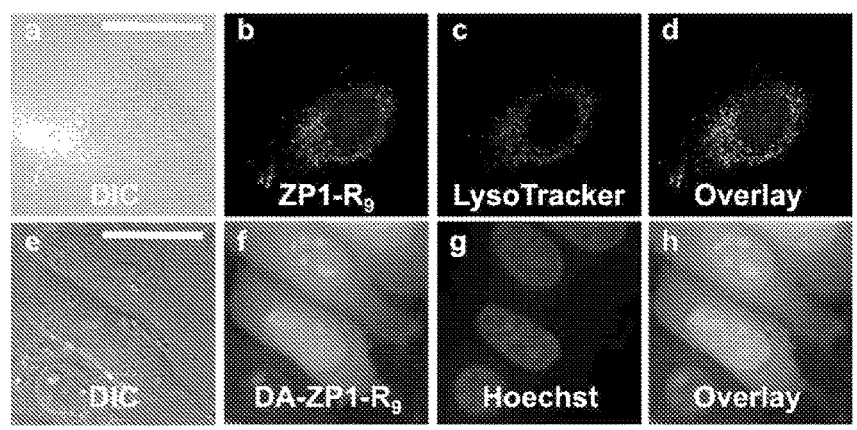
FIG. 27 depicts deconvoluted fluorescence microscopy images of live HeLa cells pretreated with ZP1-$R_9$ (5 µM) or DA-ZP1-$R_9$ (2.5 µM) and the indicated organelle stain. Top, ZP1-$R_9$: (a) Differential interference contrast (DIC) image, (b) signal from ZP1-$R_9$, (c) signal from LysoTracker Red, (d) overlay of (b) and (c). Pearson's r=0.42±0.16 (n=8). Bottom, DA-ZP1-$R_9$: (e) DIC, (f) signal from DA-ZP1-$R_9$ after treatment with 25 µM ZnPT, (g) signal from Hoechst 33258, (h) overlay of (f) and (g). Scale bar=25 µm.

For an initial targeting vector, we chose a nona-arginine (R$_9$) internalization sequence. This sequence, which has been extensively studied, delivers various cargos, including fluorescein, to the cytoplasm and nucleus. When HeLa cells were pretreated with 5 µM ZP1-R$_9$ a punctate pattern was observed throughout the cytoplasm, which co-localized moderately with endosomal tracker Dextran Red, Pearson's r=0.42±0.16 (FIG. 27, a-d). (Nomenclature describing the extent of co-localization between labelled peptides and organelle trackers was adopted from V. Zinchuk, et al. Sci. Rep., 2013, 3). Bathing cells in medium containing a zinc ionophore, zinc pyrithione (ZnPT, 25 µM), resulted in no significant increase in the fluorescence signal (data not shown). The loss of zinc response in ZP1-R$_9$ is attributed to sequestration of the probe within acidic, endocytotic vesicles. These results mirror recent work with ZP1-TPP, which revealed the propensity for ZP1 conjugates to accumulate within acidic vesicles and lose their ability to respond to zinc.

Figure 28:
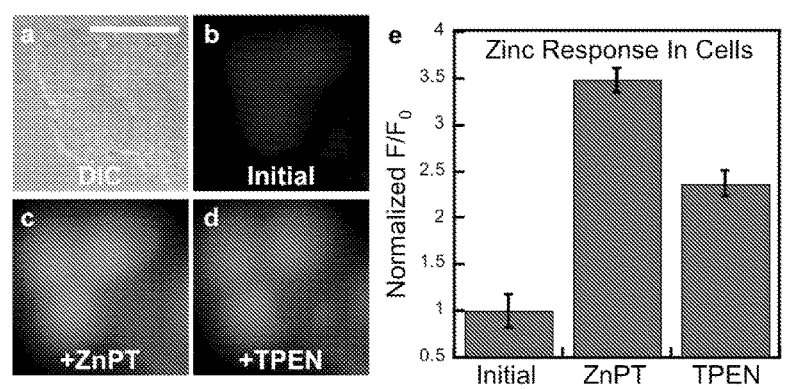
FIG. 28 depicts the response of DA-ZP1-$R_9$ to zinc pyrithione (ZnPT) in live HeLa cells. (a) Differential interference contrast (DIC) image. Signal from DA-ZP1-$R_9$ (b) initially, (c) after addition 25 µM ZnPT, and (d) after addition of 50 µM TPEN. (e) Quantification of the fluorescence response in cells normalized to initial levels. Scale bar=25 µm.

The reaction-based probe DA-ZP1-R$_9$, in contrast, was distributed throughout the cytoplasm and nucleus (FIG. 28, e-h). When cells pretreated with 2.5 µM DA-ZP1-R$_9$ were bathed in medium supplemented with 25 µM ZnPT, an approximate 3.5-fold increase in the normalized intracellular fluorescence signal was observed (FIG. 28). Addition of the intracellular chelator N,N,N',N'-Tetrakis(2-pyridylmethyl) ethylenediamine (TPEN, 50 µM) partially attenuated the fluorescence signal, presumably by removing zinc from the sensor and restoring the ability of the dipicolylamine arms to quench fluorescence via PET. Because zinc-mediated ester hydrolysis is irreversible, however, the signal cannot return to initial levels.

Figure 29:
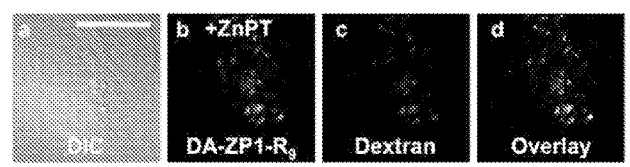
FIG. 29 depicts deconvoluted fluorescence microscopy images of live HeLa cells pretreated with 1 µM DA-ZP1-$R_9$ and 100 nM Dextran Red. (a) Differential interference contrast (DIC), (b) signal from DA-ZP1-$R_9$ after addition of 25 µM ZnPT (c) signal from Dextran Red, (d) overlay of (b) and (c). Pearson's r=0.55±0.12 (n=11). Scale bar=25 µm.
Figure 30:
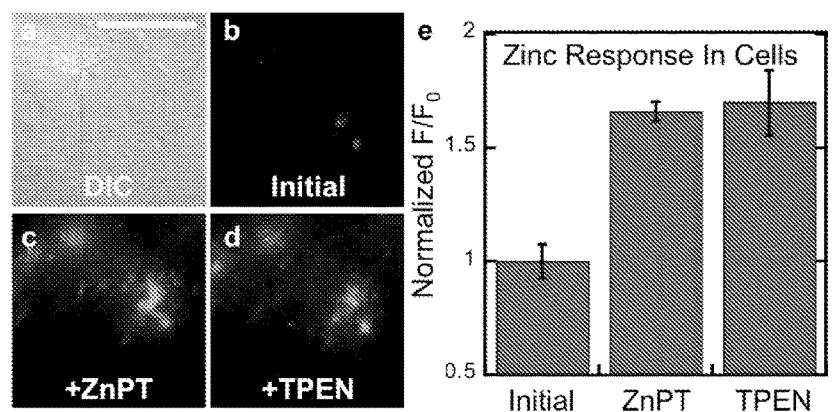
FIG. 30 depicts fluorescence microscopy of live HeLa cells pretreated with 1 µM DA-ZP1-$R_9$. (a) Differential interference contrast (DIC) image, signal from DA-ZP1-$R_9$ (b) initially, (c) after addition of 25 µM ZnPT, and (d) after addition of 50 µM TPEN. (e) Quantification of the zinc-induced fluorescence response. Scale bar=25 µm.

When HeLa cells were pretreated with medium containing 1 µM DA-ZP1-R$_9$, the sensor localized to endocytotic vesicles (FIG. 29). These results are consistent with an energy-dependent uptake mechanism, typically associated with polycationic peptides. Further support for such a mechanism is the inability of DA-ZP1-R$_9$ to penetrate the plasma membrane when incubated with live cells at 4° C. We note, however, that once the acetyl groups are removed the resulting construct, ZP1-R$_9$, is susceptible to proton-induced turn-on. Thus, addition of TPEN did not attenuate the fluorescence signal (FIG. 30). Nevertheless, these results demonstrate that peptides can be used to direct zinc sensors to vesicles, which are important targets in metalloneurochemistry.

Figure 31:
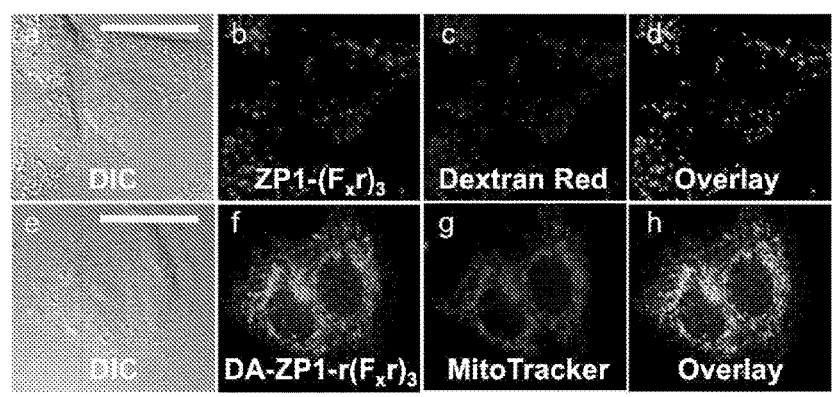
FIG. 31 depicts deconvoluted fluorescence microscopy images of ZP1-$(F_xr)_3$ and DA-ZP1-r$(F_xr)_3$ in live HeLa cells. Top, cells pretreated with medium containing 2.5 µM of ZP1-$(F_xr)_3$: (a) Differential interference contrast (DIC) image, (b) signal from ZP1-$(F_xr)_3$, (c) signal from Dextran Red, (d) overlay of (b) and (c). Pearson's r=0.71±0.07. Bottom, cells pretreated with 1 µM DA-ZP1-r$(F_xr)_3$: (e) DIC, (f) signal from DA-ZP1-r$(F_x)_3$ after treatment with 25 µM ZnPT, (g) signal from MitoTracker Red, (h) overlay of (f) and (g). Pearson's r=0.41±0.09. Scale bar=25 µm.

To investigate whether reaction-based zinc probes are compatible with other peptide constructs, we prepared mitochondrial-targeting DA-ZP1-r(F$_x$r)$_3$. The mitochondrial-penetrating peptide, (F$_x$r)$_3$, is composed of non-natural amino acids L-cyclohexylalanine (F$_x$) and D-arginine and can deliver chemotherapeutics and small-molecule fluorophores specifically to mitochondria in live cells. As was the case for ZP1-R$_9$, the non-acetylated derivative, ZP1-(F$_x$r)$_3$, was sequestered within acidic vesicles (FIG. 31, a-d) and failed to respond to zinc. We therefore prepared another construct, ZP1-r(F$_x$r)$_3$, featuring an additional N-terminal arginine to aid in mitochondrial targeting by mitigating the negative charge of the 2-carboxylate group on fluorescein. ZP1-r(F$_x$r)$_3$, however, also failed to deliver ZP1 to mitochondria (data not shown). In contrast, DA-ZP1-r(F$_x$r)$_3$ localized moderately to mitochondria at concentrations as low as 1 µM (Pearson's r=0.41±0.09) (FIG. 31e-f). We speculate that the lower Pearson's value is due to the peptide entering cells by an energy-dependent mechanism during which some portion of the construct remains sequestered within acidic vesicles. Consistent with an energy-dependent uptake mechanism is the observation that DA-ZP1-r(F$_x$r)$_3$ cannot permeate the cell membrane when incubated with live cells at 4° C.

Figure 32:
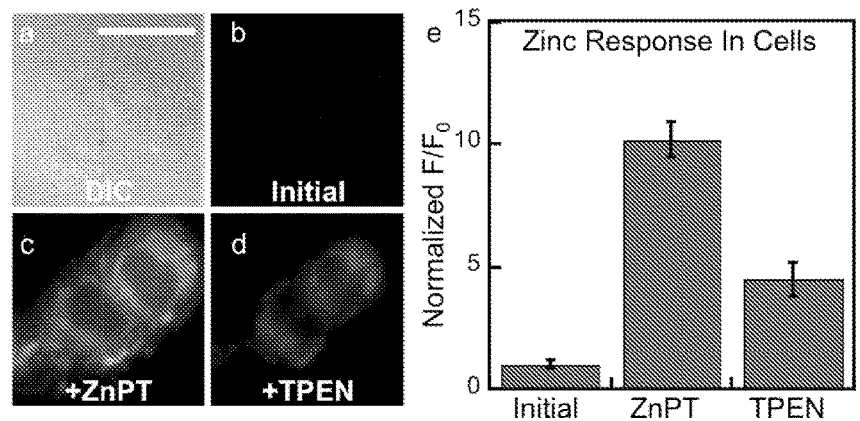
FIG. 32 depicts the response of DA-ZP1-r$(F_xr)_3$ to zinc pyrithione in live HeLa cells. (a) Differential contrast image (DIC). Signal from ZP1-$R_9$ (b) initially, (c) after addition 25 µM ZnPT, and (d) after addition of 50 µM TPEN. (e) Quantification of the fluorescence response in live HeLa cells normalized to initial level (n=9). Scale bar=25 µm

DA-ZP1-r(F$_x$r)$_3$ detects changes in mobile zinc concentration within mitochondria. When HeLa cells were pretreated with 1 µM DA-ZP1-r(F$_x$r)$_3$ and bathed in medium containing 25 µM ZnPT, a 10-fold increase in fluorescence was observed (FIG. 32). Addition of TPEN (50 µM) reduced the fluorescence signal, validating the zinc-dependent nature of the response (FIG. 32).

These results with DA-ZP1-R$_9$ and DA-ZP1-r(F$_x$r)$_3$ demonstrate that our reaction-based probes generally avoid endosomal sequestration and that peptides can be used to direct fluorescein-based zinc probes to discrete cellular locales.

Example 14

Figure 33:
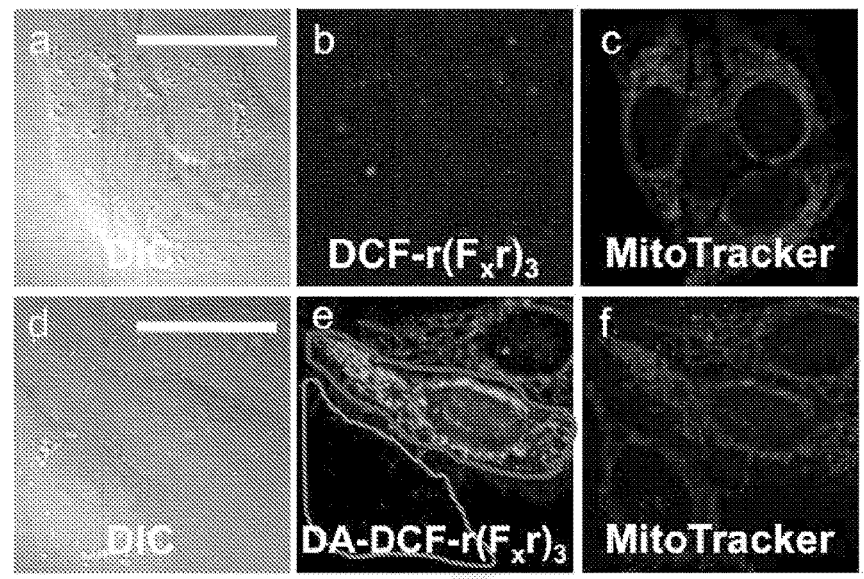
FIG. 33 depicts deconvoluted fluorescence microscopy images of DCF-r$(F_xr)_3$ and DA-DCF-r$(F_xr)_3$ in live HeLa cells. Top, cells pretreated with 5 µM DCF-r$(F_xr)_3$ and 500 nM MitoTracker Red for 30 min. (a) differential contrast image (DIC), (b) signal from DCF-r$(F_xr)_3$, (c) signal from MitoTracker Red. Bottom, cells pretreated with 5 µM DA-DCF-r$(F_xr)_3$ and 500 nM MitoTracker Red for 30 min. (d) DIC, (e) signal from DCF-r$(F_xr)_3$, (f) signal from MitoTracker Red. The global Pearson's r=0.57±0.16 (n=37). Cells with high levels of DA-DCF-r$(F_xr)_3$ (e, red outline) have a higher Pearson's r=0.83±0.08 (n=10). Scale bar=25 µm.

Peptide-Based Targeting of the Esterase-Sensitive 2',7'-Dichlorofluorescein Diacetate Given the prevalence of fluorescein-labelled peptides in biological studies and the dramatic difference in localization between acetylated versus non-acetylated ZP1-peptides, we investigated whether acetylation could improve the uptake and localization of a 2',7'-dichlorofluorescein labelled peptide. Fluorescein constructs are commonly used as fluorescent tags in order to visualize the localization of peptide constructs within live cells. Recent literature, however, reveals that fluorescein is a "non-innocent" reporter that can alter the uptake and localization of a peptide. Achieving significant uptake of fluorescein-labeled peptides often requires high loading concentrations of ≥10 µM, co-administration with endosomal disrupting agents, or modification of side chain residues. Using r(F$_x$r)$_3$ as a model system, we compared the uptake and localization of peptide derivatives labelled with 2',7'-dichlorofluorescein (DCF) or 2',7'-dichlorofluorescein diacetate (DA-DCF), respectively. DA-DCF relies on endogenous esterases to remove the acetyl groups and restore the fluorescent properties of the probe. At a concentration of 5 µM, DCF-r(F$_x$r)$_3$ failed to significantly penetrate the plasma membrane (FIG. 33a-c). DA-DCF-r(F$_x$r)$_3$, in contrast, permeated the plasma membrane and localized within mitochondria. The co-localization between MitoTracker Red and DA-DCF-r(F$_x$r)$_3$ yielded Pearson's r=0.57±0.16. A heterogeneous population distribution was observed, with some cells failing to accumulate appreciable quantities of peptide (FIG. 33e). For completeness, all cells, regardless of signal intensity, were included in the co-localization calculation. Cells with appreciable emission intensity had a significantly higher localization correlation, Pearson's r=0.83±0.08 (FIG. 33e). The reason for the heterogeneous distribution is unknown. Nonetheless, this proof-of-concept study shows that modification of the fluorescein provides a facile strategy to overcome altered localization of targeting peptides by an appended fluorophore. Because fluorescein diacetate has stability issues when incubated in complete medium, however, modification of the fluorescein with the acetoxymethyl ester group provides a more robust platform for peptide targeting in live slice and animal studies.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by Formula 1 or Formula 2 or Formula 3:

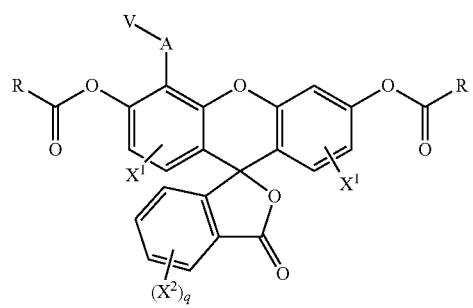

Formula 1

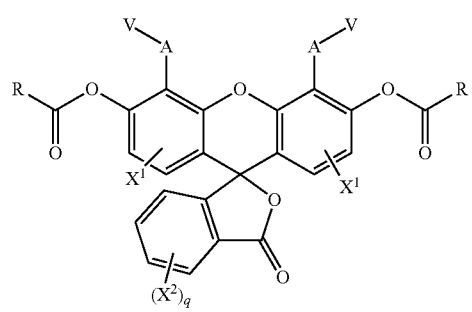

Formula 2

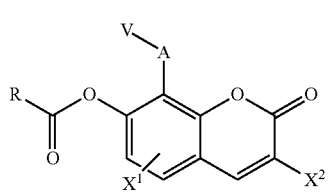

Formula 3 wherein, independently for each occurrence,

X$^1$ is —H, —F, or —Cl;
X$^2$ is —F, —Cl, —CO$_2$R$^1$, —C(O)-linker, -linker, —NR$^1$-linker, or —S-linker, wherein the linker, when present, is a linker to a first amino acid or a lipophilic group;
R is alkyl or aryl;
R$^1$ is —H or alkyl;
q is 0, 1, 2, 3, or 4;
A is an alkylene group; and
V is a Lewis base.

2. The compound of claim 1, wherein q is 0 or 1.

3. The compound of claim 1, wherein A is substituted or unsubstituted methylene or substituted or unsubstituted ethylene.

4. The compound of claim 1, wherein V is —N(R$^3$)$_2$; and R$^3$ is independently —H, alkyl, aryl, heteroaryl, aralkyl, heteroaralkyl, alkoxyalkyl, or alkylthioalkyl.

5. The compound of claim 1, wherein the compound is selected from the group consisting of

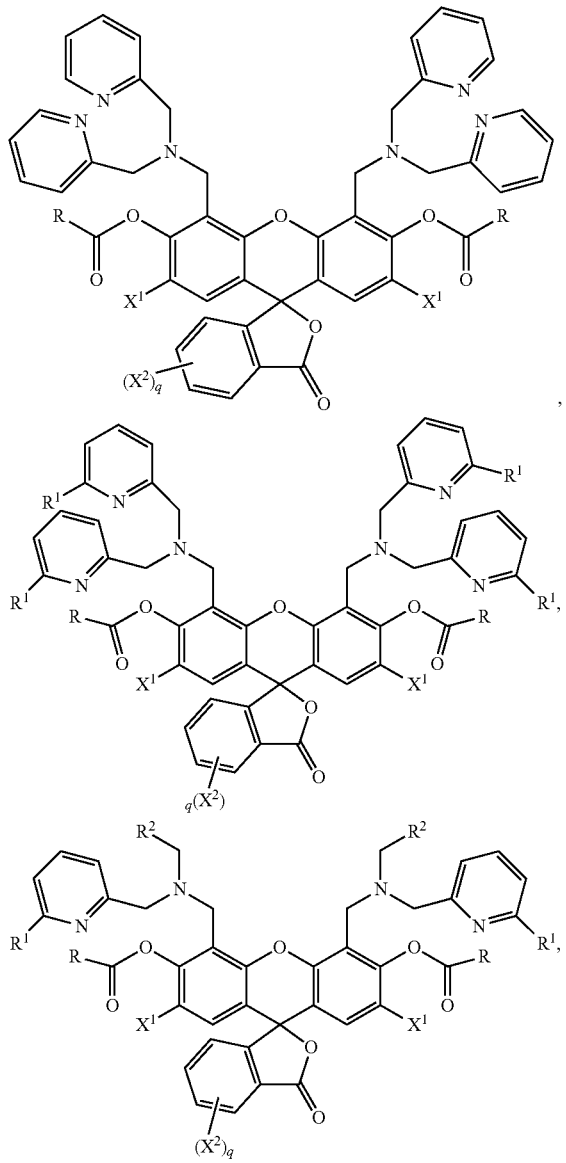

31
-continued
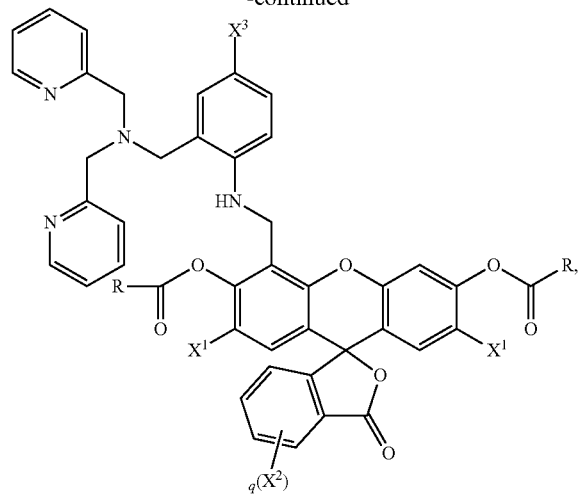
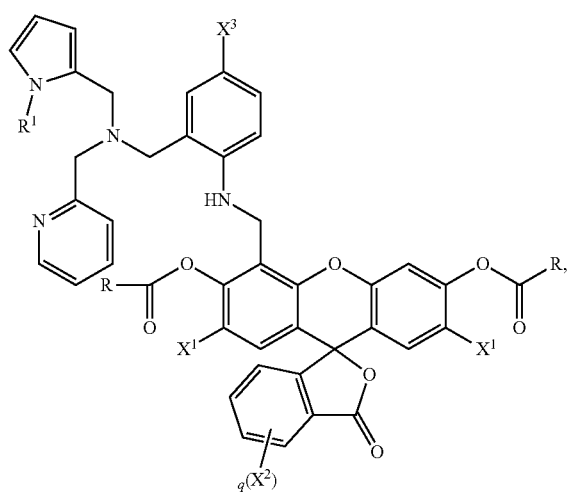
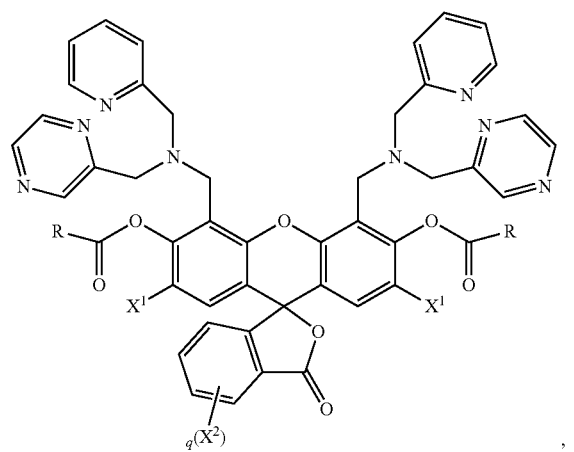
32
-continued
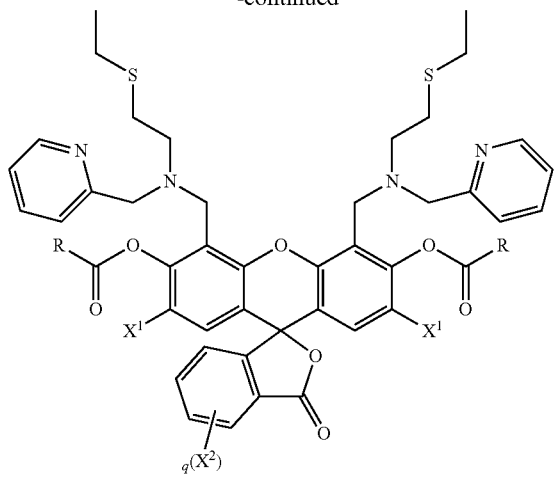
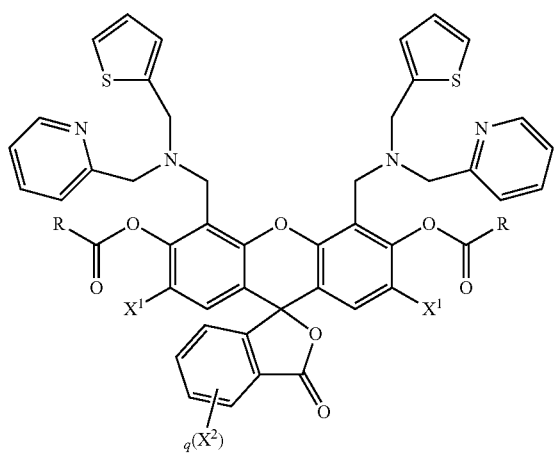
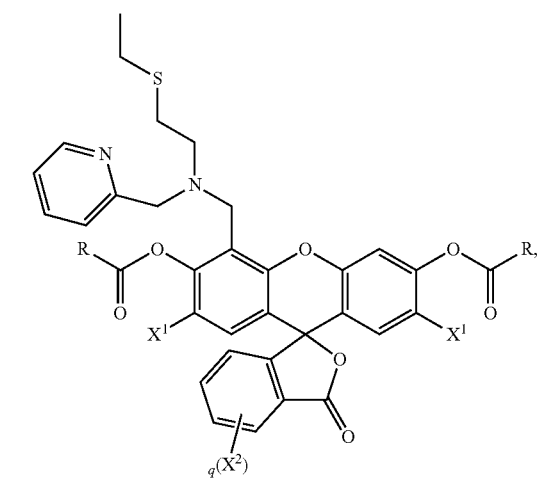

-continued

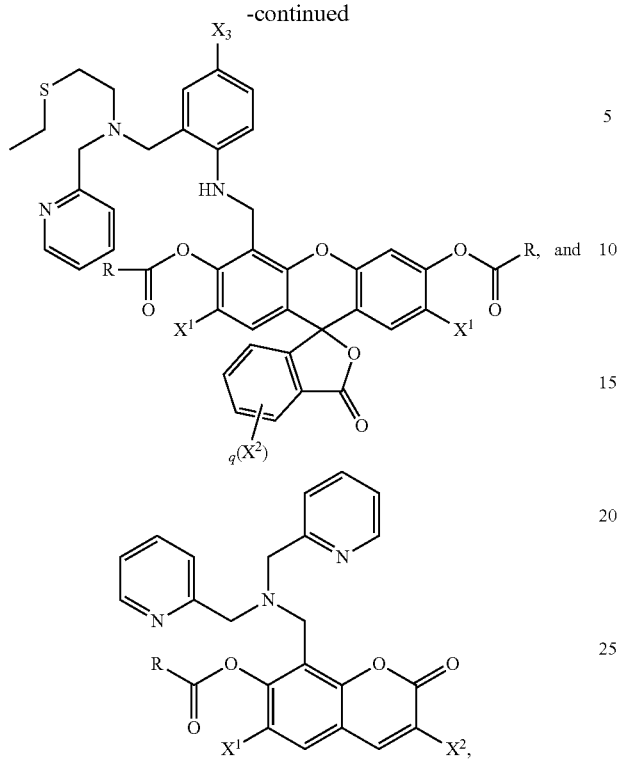

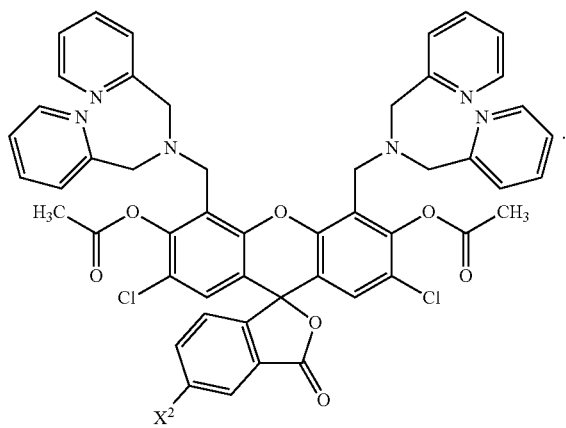

wherein, independently for each occurrence,
X³ is —H, —F, —Cl, or —OR¹; and
R² is —H or phenyl.

6. The compound of claim 1, wherein q is 1; and X² is —C(O)-linker.

7. The compound of claim 1, wherein R is alkyl.

8. The compound of claim 1, wherein the compound is

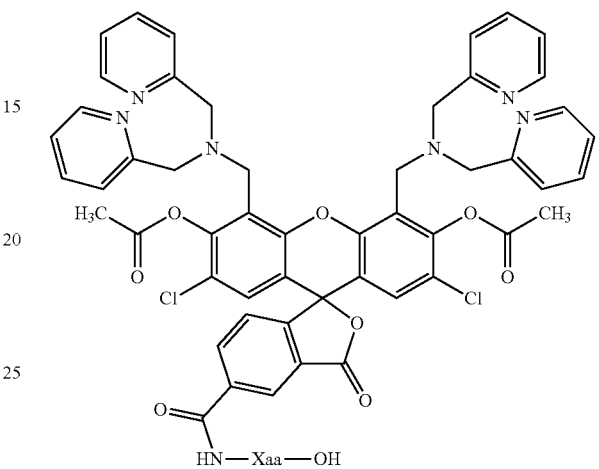

9. The compound of claim 1, wherein X² is —C(O)-linker, -linker, —NR¹-linker, or —S-linker; the linker is a linker to a first amino acid; and the first amino acid is a natural α-amino acid or a non-natural α-amino acid.

10. The compound of claim 1, wherein X² is —C(O)-linker, -linker, —NR¹-linker, or —S-linker; the linker is a linker to a first amino acid; and the first amino acid is D-arginine.

11. The compound of claim 1, wherein X² is —C(O)-linker, -linker, —NR¹-linker, or —S-linker; and the linker is an amide bond, a disulfide bond, a thioether bond, a thiourea, or a triazole.

12. The compound of claim 1, wherein X² is —C(O)-linker, -linker, —NR¹-linker, or —S-linker; and the linker is an amide bond.

13. The compound of claim 1, wherein the compound is:

wherein Xaa is a natural amino acid or a non-natural amino acid.

14. The compound of claim 13, wherein Xaa is arginine.

15. A method of quantifying an amount of a substance in a cell, comprising the steps of:
   contacting the cell with a detectable amount of a compound of claim 1; and
   detecting a signal, wherein the signal emitted by the compound in the presence of the substance is different than the signal emitted by the compound in the absence of the sub stance.

16. The method of claim 15, wherein the method is a method of quantifying an amount of a substance in a specific locale of a cell, wherein the signal is detected from a specific locale of the cell.

17. The method of claim 16, wherein the specific locale in the cell is an intracellular probe, an extracellular probe, a trans-Golgi network, a mitochondrion, or an endoplasmic reticulum.

18. The method of claim 15, wherein the substance is $Zn^{2+}$.

19. A method of quantifying an amount or determining a location of a substance in a subject, comprising the steps of:
   administering to the subject a detectable amount of a compound of claim 1; and
   detecting a signal, wherein the signal emitted by the compound in the presence of the substance is different than the signal emitted by the compound in the absence of the substance.

20. The method of claim 19, wherein the location of the substance is the synaptic cleft, the intracellular space of the hippocampus, in mossy fiber buttons of the hippocampus, the pancreas, the prostate, or the prostatic fluid.

21. The method of claim 19, wherein the substance is Zn$^{2+}$.
22. A compound selected from the group consisting of
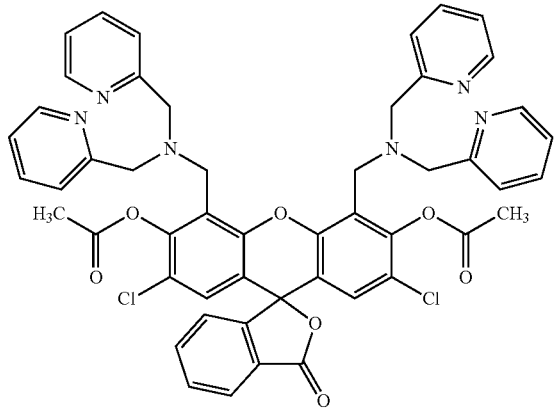
,
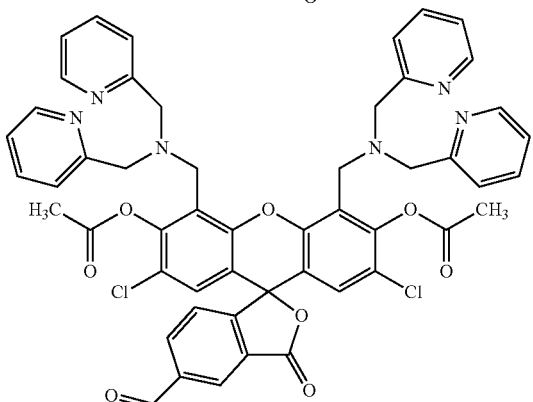
,
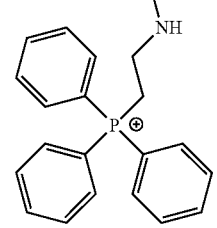
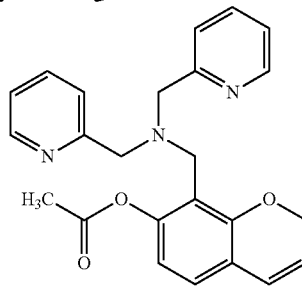
,
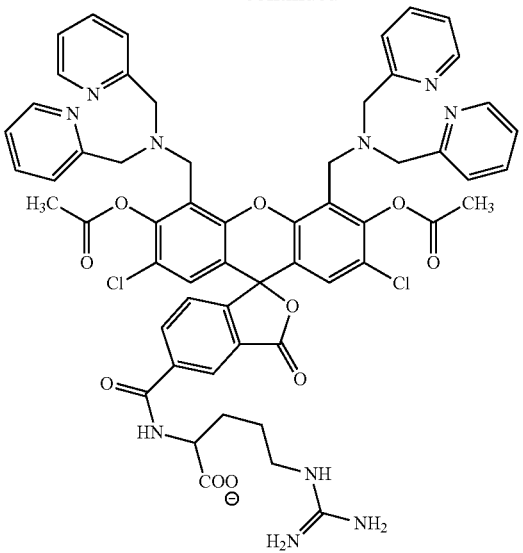
, and
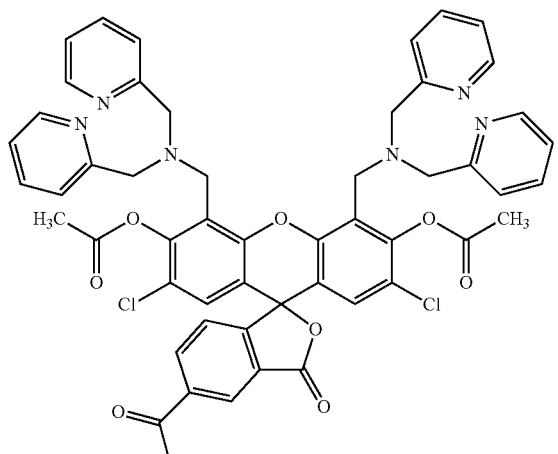
,
wherein r is D-arginine; and $F_X$ is L-cyclohexylalanine.
* * * * *